United States Patent
Swerdloff (12)

(10) Patent No.: US 11,253,728 B2
(45) Date of Patent: Feb. 22, 2022

(54) SYSTEMS AND METHODS FOR MAGNETIC FIELD LOCALIZATION OF CHARGED PARTICLE BEAM END POINT

(71) Applicant: Elekta Pty Ltd., Auckland (NZ)

(72) Inventor: Stuart Julian Swerdloff, Dunedin (NZ)

(73) Assignee: Elekta Pty Ltd., Auckland (NZ)

( * ) Notice: Subject to any disclaimer, the term of this patent is extended or adjusted under 35 U.S.C. 154(b) by 151 days.

(21) Appl. No.: 16/489,515

(22) PCT Filed: Jul. 27, 2017

(86) PCT No.: PCT/NZ2017/050105
§ 371 (c)(1),
(2) Date: Aug. 28, 2019

(87) PCT Pub. No.: WO2018/182429
PCT Pub. Date: Oct. 4, 2018

(65) Prior Publication Data
US 2020/0016431 A1    Jan. 16, 2020

Related U.S. Application Data

(60) Provisional application No. 62/477,071, filed on Mar. 27, 2017.

(51) Int. Cl.
*A61N 5/10* (2006.01)
*G01R 33/10* (2006.01)

(52) U.S. Cl.
CPC ......... *A61N 5/1067* (2013.01); *A61N 5/1038* (2013.01); *G01R 33/10* (2013.01); *A61N 2005/1087* (2013.01)

(58) Field of Classification Search
CPC .... A61N 2005/1087; A61N 2005/1085–1098; A61N 5/10–1084; G01R 33/0005; G01R 33/0094
See application file for complete search history.

(56) References Cited

U.S. PATENT DOCUMENTS 6,745,072 B1\* 6/2004 Badura ............... A61N 5/1048
607/2
2011/0006224 A1\* 1/2011 Maltz .................... A61N 5/103
250/492.3

(Continued)

FOREIGN PATENT DOCUMENTS

CN    103228319    7/2013
CN    103954789    7/2014

(Continued)

OTHER PUBLICATIONS

"European Application Serial No. 17751154.0, Response to Communication pursuant to Rules 161(1) and 162 EPC filed May 5, 20", 17 pgs.

(Continued)

*Primary Examiner* — Thaddeus B Cox
(74) *Attorney, Agent, or Firm* — Schwegman Lundberg & Woessner, P.A.; Sanjay Agrawal

(57) ABSTRACT

Embodiments of the present disclosure are directed to radiotherapy systems. An exemplary radiotherapy system may comprise a radiotherapy output configured to deliver a charged particle beam to a patient. The system may also comprise a detector array. The detector array may have an axis that extends parallel to an axis along which the charged particle beam is delivered by the radiotherapy output. The detector array may comprise a plurality of detectors configured to detect a magnetic field generated by the charged particle beam during delivery of the charged particle beam from the radiotherapy output.

21 Claims, 11 Drawing Sheets

(56) References Cited

U.S. PATENT DOCUMENTS

| | | | |
|---|---|---|---|
| 2011/0186746 A1 | | 8/2011 | Drees et al. |
| 2015/0087882 A1* | | 3/2015 | Pausch .................. A61N 5/1067 600/1 |
| 2015/0297917 A1 | | 10/2015 | Beekman et al. |
| 2017/0197097 A1* | | 7/2017 | Michaud .................. G21K 5/04 |
| 2018/0078791 A1* | | 3/2018 | Jung .................... A61N 5/1084 |

FOREIGN PATENT DOCUMENTS

| | | |
|---|---|---|
| CN | 104136077 | 11/2014 |
| CN | 104707267 | 6/2015 |
| CN | 105920744 | 9/2016 |
| GN | 110740782 | 1/2020 |
| WO | 2005076039 | 8/2005 |
| WO | WO-2018182429 A1 | 10/2018 |

OTHER PUBLICATIONS

"Chinese Application Serial No. 201780089073.4, Office Action maildated Dec. 16, 2020", w English Translation, 24 pgs.

"Chinese Application Serial No. 201780089073.4, Response filed Mar. 4, 2021 to Office Action dated Dec. 16, 20", w English claims, 13 pgs.

"International Application Serial No. PCT/NZ2017/050105, International Search Report dated Dec. 15, 2017", 4 pgs.

"International Application Serial No. PCT/NZ2017/050105, Written Opinion dated Dec. 15, 2017", 7 pgs.

Fernandes, M, et al., "Non-perturbative measurement of low-intensity charged particle beams", Superconductor Science and Technology, IOP Publishing, Techno House, Bristol, GB, vol. 30, No. 1,, (Nov. 2, 2016), 15001.

Groeger, S, et al., "Laser-pumped cesium magnetometers for high-resolution medical and fundamental research", Sensors and Actuators A: Physical, Elsevier BV, NL, vol. 129, No. 1-2,, (May 24, 2006), 1-5.

Kin, Li, et al., "High linear dynamic range magnetometer utilizing a large array of serially connected Squids", IEEE Transactions on Applied Superconductivity, IEEE Service Center, Los Alamitos, CA, US, vol. 7, No. 2, (Jun. 1, 1997), 3217-3219.

"European Application Serial No. 21166265.5, Extended European Search Report dated Jul. 12, 2021", 11 pgs.

* cited by examiner

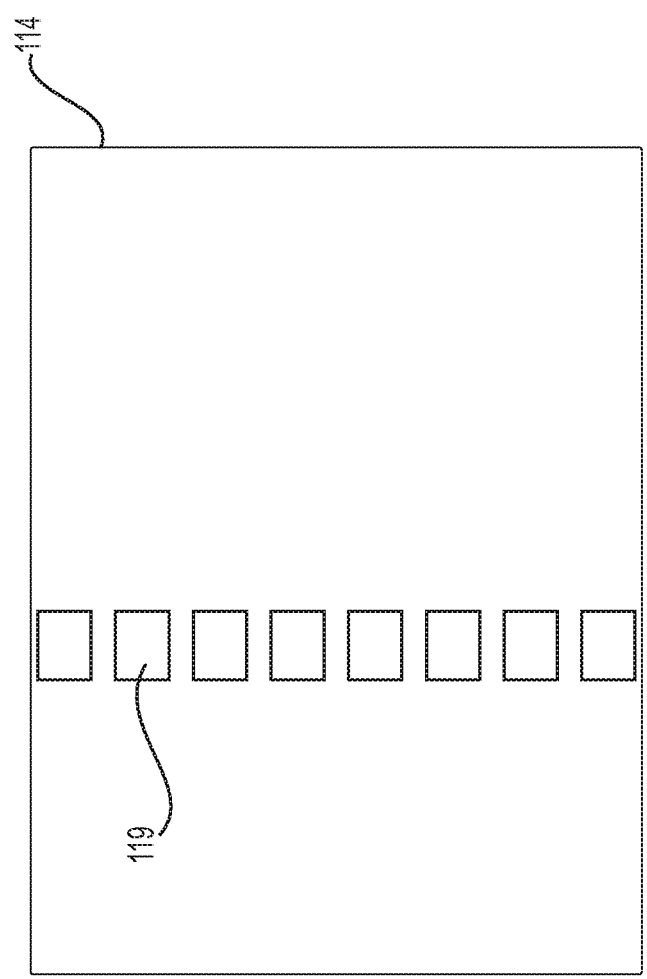

SYSTEMS AND METHODS FOR MAGNETIC FIELD LOCALIZATION OF CHARGED PARTICLE BEAM END POINT

PRIORITY APPLICATIONS

This application is a U.S. National Stage Filing under 35 U.S.C. 371 from International Application No. PCT/NZ2017/050105, filed on Jul. 27, 2017, and published as WO2018/182429 on Oct. 4, 2018, which claims the benefit of priority to U.S. Application No. 62/477,071, filed on Mar. 27, 2017; the benefit of priority of each of which is hereby claimed herein, and which applications and publication are hereby incorporated herein by reference in their entirety.

TECHNICAL FIELD

Aspects of the present disclosure relate generally to radiotherapy treatment systems, and, specifically, to methods and systems for using magnetic field localization to determine the end point of one or more charged particle beams of radiation administered during radiotherapy.

BACKGROUND

Radiation therapy (also referred to as radiotherapy) may be used in the treatment of cancer or other pathologies. Radiotherapy involves delivering a prescribed dose of radiation to a target region of a patient, for example, to a tumor or other cancerous tissue. The target region may be imaged prior to the administration of radiotherapy, and a treatment plan may be formulated based on, e.g., the size, location, and/or orientation of the target and the surrounding structures, among other things. A radiotherapy delivery device may then be used to deliver radiation in the form of one or more charged particle beams to the target region of the patient, in accordance with the treatment plan.

Accurate delivery of radiation to a patient promotes the safety and efficacy of radiotherapy treatment. Accordingly, prior to treatment, attenuation of a charged particle beam within the patient is predicted in order to determine where radiation will and will not be delivered to the body during treatment. Accurate determination of the location of the distal edge of a charged particle beam allows healthcare providers to assess how much dose was delivered to a patient and where the dose was delivered. The intended location of the distal end of the beam and the dose delivered may be selected to ensure that surrounding healthy cells are not harmed or killed. If the charged particle beams delivered during radiotherapy have end points that are positioned in different locations than intended, then surrounding healthy structures may receive radiation instead of, or in addition to, the intended target region, and/or the target region may receive a different dose of radiation than intended. As a result, it is desirable to know the location of the actual, in vivo end point of a charged particle beam during treatment and to know how the actual location compared to the predicted end point location. Further, it may be desirable to assess the beam end point location during treatment so that the radiotherapy treatment may be altered or stopped if the actual, in vivo beam end point is not in the intended location.

Currently available technology for determining the actual, in vivo beam end point location of a charged particle beam may lack accuracy and may not provide information in a timely manner to be a useful assessment tool during treatment. For example, positron emission tomography (PET) may be used to determine tissue activation by a radiation particle beam in vivo. Yet, activation of the tissue may not provide a sufficiently accurate representation of the dose distribution of a charged particle beam or of the end terminus of the particle beam. Additionally, PET information may not be accessible in a timely manner. For example, it may take several minutes or more to acquire PET data.

Accordingly, a need exists for systems and methods that allow for the accurate, real-time determination of the location of the end point of a charged particle beam during the administration of radiotherapy.

SUMMARY

Embodiments of the present disclosure are directed to radiotherapy systems. An exemplary radiotherapy system may comprise a radiotherapy output configured to deliver a charged particle beam to a patient. The system may also comprise a detector array. The detector array may have an axis that extends parallel to an axis along which the charged particle beam is delivered by the radiotherapy output. The detector array may comprise a plurality of detectors configured to detect a magnetic field generated by the charged particle beam during delivery of the charged particle beam from the radiotherapy output.

Various embodiments of the system may include one or more of the following features. The radiotherapy output may be configured to deliver a proton beam. In some aspects, the plurality of detectors may comprise at least one of a superconducting quantum interference device, a laser-pumped detector, or a magnetometer, and at least one detector of the plurality of detectors may be oriented so that a planar surface of the at least one detector is oriented at an angle transverse to the axis of detector array. The plurality of detectors may be interdigitated relative to one another. The system may include a plurality of detector arrays, the detector array may be a two-dimensional detector array, and/or the plurality of detectors may be movably mounted on the detector array.

Embodiments of the present disclosure are also directed to systems for measuring an end point of a charged particle beam during radiotherapy treatment. An exemplary system may comprise at least one computer configured to receive a signal indicative of a magnetic field detected by a detector, and, based on the received signal, determine an in vivo location of the end point of the charged particle beam. The at least one computer may also be configured to continue, modify, or stop the radiotherapy treatment based on the in vivo location of the end point of the charged particle beam.

Various embodiments of the system may include one or more of the following features. The at least one computer system may further be configured to compare the in vivo location of the end point of the charged particle beam to an intended location of the end point of the charged particle beam calculated prior to delivery of the charged particle beam. In some aspects, the at least one computer system may also be configured to stop or modify the radiotherapy treatment if the in vivo location of the end point of the charged particle beam is outside of a threshold level of error relative to the intended location of the end point of the charged particle beam, and continue the radiotherapy treatment if the in vivo location of the end point of the charged particle beam is within the threshold level of error relative to the intended location of the end point of the charged particle beam. The at least one computer system may also be configured to update at least one of a stopping power map, a record of the plan as-delivered, or a treatment record to include the in vivo location of the end point of the charged particle beam. Further, the at least one computer system may be configured to modify a future radiotherapy treatment session based on the in vivo location of the end point of the charged particle beam.

Embodiments of the present disclosure are also directed to a radiotherapy system comprising a detector array having a length positioned parallel to an axis along which a charged particle beam is delivered. The detector array may comprise a plurality of detectors configured to detect a magnetic field generated by the charged particle beam. The plurality of detectors may also be spaced apart from one another along the length of the detector array and along the axis along which the charged particle beam is delivered.

Various embodiments of the system may include one or more of the following features. The plurality of detectors may comprise at least one of a superconducting quantum interference device, a laser-pumped detector, or a magnetometer. The at least one detector of the plurality of detectors may be oriented so that a planar surface of the at least one detector is oriented at an angle transverse to an axis of the detector array. The plurality of detectors may also extend along a width of the detector array, and/or the plurality of detectors may be interdigitated relative to one another. In some aspects, the detector array may be a first detector array, and the system may further comprise a second detector array. The second detector array may be positioned orthogonal to the first detector array.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings:

FIG. 2A schematically depicts a detector array, according to various embodiments of the present disclosure.

DETAILED DESCRIPTION

Figure 1:
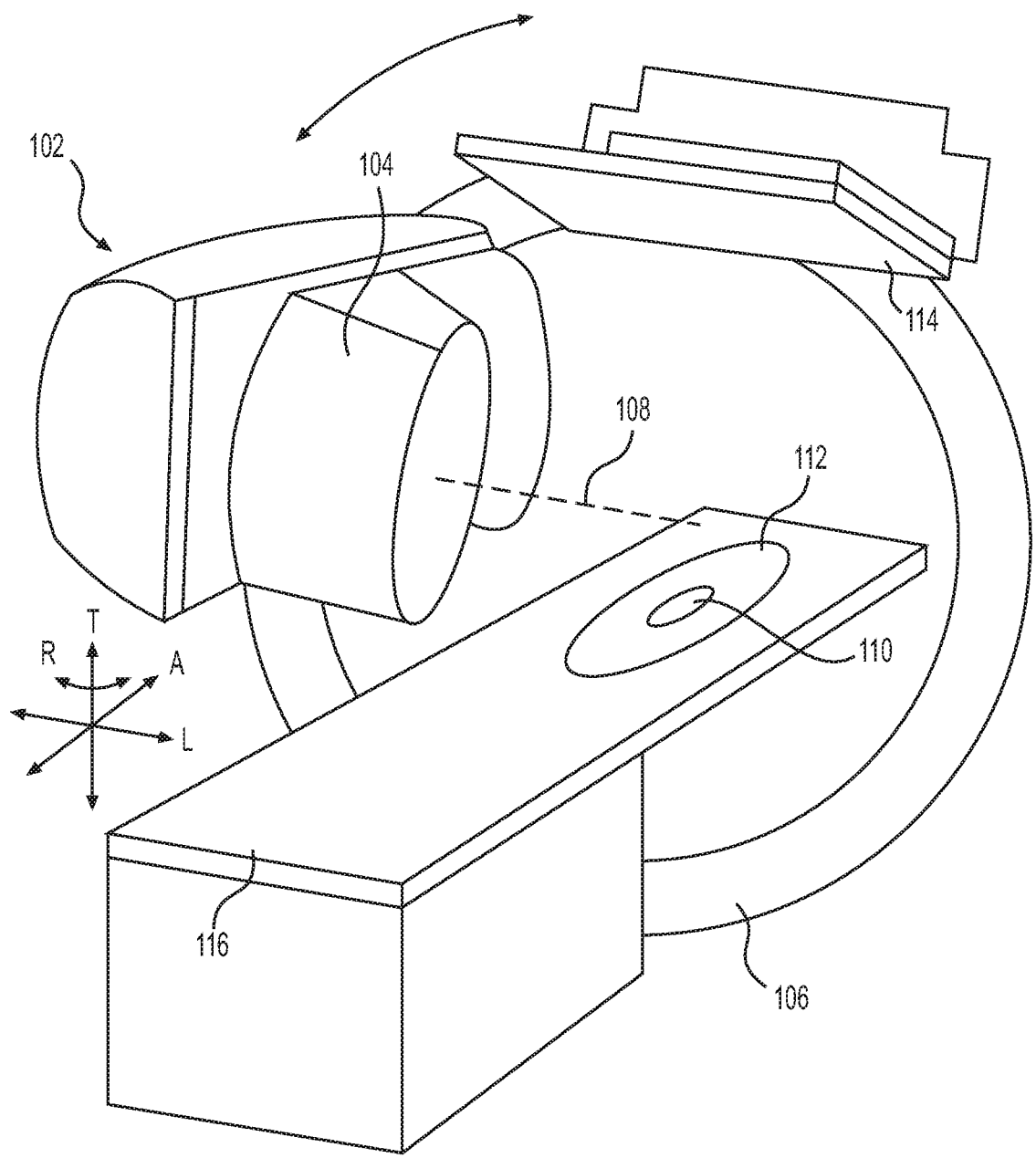
FIG. 1 depicts an exemplary radiotherapy device, according to various embodiments of the present disclosure.

Reference will now be made in detail to the exemplary embodiments of the present disclosure described below and illustrated in the accompanying drawings. Wherever possible, the same reference numbers will be used throughout the drawings to refer to same or like parts. The term "exemplary" is used in the sense of "example," rather than "ideal." The term "approximately" is used to mean within a range of 10% of the number it modifies. As used herein, the term "real time" means that the magnetic field of a charged particle beam is detected and/or data is processed at a speed that allows output or feedback to be made available during the course of a radiotherapy session, otherwise referred to as a fraction. In some embodiments, this may mean that detection occurs and a charged particle beam end point location is generated within, e.g., several milliseconds, within several hundred milliseconds, or within several seconds. In some embodiments, the speed of detection and/or any related data processing may depend, at least in part, on the location of the target region being treated, the depth of the charged particle beam, the energy or intensity of the charged particle beam, the type of charged particle beam, the type of radiation delivery device, the number or type of magnetic field detectors, and/or any other suitable factors or combination of factors.

As used herein, the terms "beam end point" and "beam terminus" refer to the location of the Bragg peak, as will be described further below. It is acknowledged that in some aspects, a charged particle beam may not have an abrupt, complete end point, and that a dissipated portion of the beam may extend further than the Bragg peak, but for the purposes of this disclosure, the end of the beam will be understood to refer to the location of the Bragg peak. Although many of the exemplary embodiments of the present disclosure refer to proton beam radiation delivery devices and/or pencil beam radiation, it will be understood by those of ordinary skill in the art that the disclosed embodiments may be used in combination with any suitable type of charged particle beam radiotherapy system. For example, embodiments of the disclosure may be used in conjunction with various types of charged particle beam delivery devices, including electron beam, ion beam (e.g., carbon, helium, neon, or silicon ions), or other suitable charged particle beam radiation delivery devices.

Additionally, charged particle beam radiation may be used to treat a variety of cancers, including, e.g., prostate cancer; bladder cancer; uterine cancer (including uterine cervix and body); ocular cancer (including uveal melanoma, metastasis to the retina, and conjunctival cancer); head and neck cancers (including malignancies of the brain like glioblastomas, of the skull base cervical spine, and other malignancies like the sinonasal tract); spinal cancer (including sacral tumors, chordomas, and chondrosarcomas); gastrointestinal cancers (including liver, esophageal, pancreatic, and bile duct tumors); bone and soft tissue cancers; lung cancer; breast cancer; skin cancer; and other cancers.

As discussed above, accurate, real-time determination of the end point of one or more charged particle beams delivered during the administration of radiotherapy may allow healthcare providers to better assess where radiation is being delivered and at what dose. Charged particle beams have different depth-dose distributions compared to photon beams delivered by other radiotherapy devices. Charged particle beams deposit most of their energy at the end region of their trajectory, e.g., the last final millimeters, as their speed through the body slows. This results in a localized peak of radiation dose, referred to as the Bragg peak. As a result, charged particle beams deposit little radiation to normal tissues located in front of or beyond the Bragg peak, and the Bragg peak can be aligned with the location of a target region. By controlling the distal end of the trajectory of a particle beam (i.e., where the Bragg peak occurs), a target region within the body may be precisely targeted with radiation.

The initial speed (energy) of the charged particle beam determines how deep within the body the Bragg peak will form, and the intensity of the charged particle beam determines the dose of radiation deposited within the body. The speed and intensity of the particles may be manipulated to adjust the location and dose of radiation delivered to a patient. To irradiate a target region within the body, beams of different speed and intensity may be delivered to create Bragg peaks at different locations within the body so that radiation is delivered to different areas of the target region with each beam. Accurate dose delivery depends on accurately controlling where the radiation is delivered, i.e., where the beam terminates and the Bragg peak forms. Yet the predicted locations of beam termination calculated during treatment planning may differ from the actual beam termination locations during delivery of radiotherapy. Accordingly, accurate, real-time measurement of the location of one or more charged particle beam end points is needed.

Uncertainty regarding the actual location of a beam end point in vivo is due primarily to uncertainty regarding the particle-stopping power of tissue positioned between the entry point of the charged particle beam within the body and the target region and/or the tissue of the target region itself. For example, inconsistencies within tissue—like air pockets or changes in tissue density—may affect the location of dose deposition. The stopping power in vivo may be estimated prior to the administration of radiotherapy based on one or more computerized tomography (CT) scans, magnetic resonance imaging (MRI) scans, ultrasound scans, or any other suitable medical imaging of the patient. Modeled conversion of the imaging scan values relative to the stopping power values may be performed, but both the measured values and the model for mapping may be inherently uncertain, resulting in an inaccurate assessment of dose delivery.

Embodiments of this disclosure are drawn to systems and methods of measuring a charged particle beam terminus in vivo by detecting the magnetic field generated by the charged particle beam as the beam is being delivered to a patient. Being able to generate real-time beam end point location information may allow healthcare providers to more accurately track the location of the beam end point during treatment. It may also allow providers to modify and/or stop the current treatment session and/or modify future treatment sessions in response to deviations between the intended beam end point location and the actual beam end point location delivered during treatment, as measured by the systems and methods described herein.

Exemplary Systems

Particle beam radiotherapy may be delivered in a number of different ways. For example, intensity modulated proton therapy (IMPT) may be used to deliver a narrow proton beam, commonly referred to as a 'pencil beam' or a 'spot scan,' to a target region via use of a magnetic field. The intensity of the beam and speed (i.e., energy) of the protons in each charged particle beam may be modulated in order to control the location and dose of radiation being delivered with each beam.

Charged particles for delivery may first be generated by an ion source. The type of ion source used may be specific to the type of charged particle being generated (e.g., protons, electrons, carbon ions, etc.). An accelerator may then be used to accelerate the charged particles to higher energies, e.g., above approximately 50 MeV. For example, energies may exceed 200 MeV, e.g., from approximately 230 to approximately 250 MeV or higher, and may exceed 400 MeV, e.g., 430 MeV. Exemplary accelerators may include cyclotrons, synchrotrons or synchrocyclotrons, dielectric wall accelerators, fixed-field alternating gradient accelerators, or laser proton accelerators. Once the charged particles are energized, the accelerated particle beam may be transported via one or more conduits, shaping magnets, and/or focusing magnets. In some embodiments, devices, e.g., range shifters, ion range compensators, and/or wedges, may be used to decrease particle speed (i.e., particle energy).

A charged particle beam may be delivered to a patient using either a fixed-beam radiation delivery device or via a delivery device having a rotational gantry. A fixed beam may be delivered at a horizontal, vertical, or intermediate angle to a patient. With a gantry, the beams may be delivered up to 360 degrees around the patient. Either the beams may be delivered as the gantry rotates, or the gantry may be rotated to a specific angle relative to the patient, and then the beams may be delivered from that angle, or a combination of both. The particle beams may be delivered either by passive spreading (either single or dual scattering) or active spreading, also referred to as beam scanning. With passive spreading, the radiation delivery device may include one or more collimators or compensators configured to shape the particle beam. For example, the particle beams may be shaped according to the shape, volume, and/or orientation of the tumor. With beam scanning, the radiation delivery device may include one or more magnets to deflect and steer the particle beams.

In some embodiments, one or more components of the radiation therapy delivery device may be located remote from the room in which the patient is contained. In some embodiments, each of the components may be located within the same room in which the patient is contained. For example, in some embodiments, the ion source and/or accelerator may be located remote from the patient, and one or more conduits, shaping magnets, focusing magnets, electronics, wedges, and/or other suitable devices may be used to transfer the particles from the accelerator to the radiation delivery device. In some exemplary arrangements, a single ion source and/or accelerator may supply multiple radiation therapy systems, which may each be located in different patient rooms or areas.

FIG. 1 depicts an exemplary particle beam radiation therapy system 102 configured to deliver one or more charged particle beams of radiation to a patient. In some aspects, radiation therapy system 102 may be configured to deliver a pencil beam of protons. A pencil beam may be delivered from radiation therapy system 102 using magnetic or electrostatic field controls (not shown) to generate a charged particle beam having a predetermined trajectory and a predetermined particle energy. Radiation therapy system 102 may be part of a larger imaging and radiotherapy system. For example, radiation therapy system 102 may operate independently or may operate in conjunction with an imaging acquisition system, for example, an MR imaging, X-ray imaging, CT imaging, ultrasound, or any other suitable medical imaging acquisition system. One or more components of an imaging system may acquire images before, during, and/or after radiotherapy treatment.

Radiation therapy system 102 may be used to provide real-time monitoring of the locations of the end points of emitted charged particle beams during radiotherapy, in accordance with various aspects of the disclosure. The systems may use information gleaned from detector array 114 of radiation therapy system 102 to track the locations of the end points of delivered particle beams in real time and/or to control or adapt a radiation therapy treatment plan in real time, as described further below.

System 102 may include a radiation therapy output 104 configured to deliver a charged particle beam of radiation 108 to a portion of a patient located in region 112. Radiation therapy output 104 may include one or more collimators, such as a multi-leaf collimator (MLC), or compensators. Collimators and/or compensators may be used to shape particle beam 108, e.g., based on the size and/or shape of the target region.

System 102 may also include a surface 116, for example, a table, bed, or couch, and a patient or a portion of a patient may be positioned on region 112 of surface 116 to receive a prescribed radiation therapy dose according to a radiation therapy treatment plan. In some embodiments, surface 116 may move relative to system 102. For example, surface 116 may move in a transverse (T) direction, a lateral direction (L), an axial direction (A), and/or may rotate about a transverse axis (R), e.g., to assist with moving the patient into and out of system 102, positioning the patient within system 102, setting up system 102, and/or cleaning or repairing system 102.

Radiation therapy output 104 may be coupled to a gantry 106 or other mechanical support and may be configured to move relative to the patient, relative to system 102, and/or relative to gantry 106. For example, radiation therapy output 104 may rotate on gantry 106 around an axis (A) extending through a central region of gantry 106. Radiation therapy output 104 may additionally or alternatively be movable in a transverse direction or a lateral direction. This may, e.g., allow radiation therapy output 104 to be positioned relative to the patient. In some embodiments, radiation therapy system 102 may not include a gantry 106, and the location of radiation therapy output 104 may be fixed in place or may move less than 360 degrees around a patient positioned on surface 116.

One or more of surface 116, radiation therapy output 104, and/or gantry 106 may be manually or automatically positioned relative to one another in system 102. Characteristics of charged particle beam 108 output by radiation therapy output 104 may be manually or automatically controlled and may be determined according to a specified dose of radiation intended for a specific region of interest of the patient for a particular radiotherapy delivery session during a treatment plan. A sequence of radiation therapy deliveries may be specified according to a radiation therapy treatment plan, for example, one or more different orientations or locations of gantry 106, surface 116, and/or radiation therapy output 104 may be adjusted based on the sequence. For example, radiation therapy output 104 may move along gantry 106 around axis A and may output one or more particle beams 108 at a number of different locations. Thus, charged particle beams 108 from radiation therapy output 104 may be delivered to the target region from a number of different directions. In some embodiments, deliveries of radiation therapy from different angles may occur sequentially but each may end at region of interest 110. In this way, a prescribed cumulative dose of radiation therapy may be delivered to a target region within the patient from different angles. During delivery, exposure and damage to structures surrounding the target region may be reduced or avoided with precise delivery of radiation by, e.g., controlling the position of radiation therapy output 104, the energy of charged particle beams 108, and/or the intensity of the charged particle beams 108.

Detector Arrays and Beam End Point Detection

Detector array 114 may be mounted on gantry 106 approximately 90 degrees away from radiation therapy output 104 and may move with radiation therapy output 104 to maintain alignment above charged particle beams 108 as gantry 106 rotates. In some aspects, detector array 114 may be movably mounted (either automatically or manually movable) on radiotherapy system 102. For example, detector array 114 may be moved closer to or further from the patient to position detector array 114 relative to the patient once the patient is arranged on surface 116. If the orientation of radiation therapy output 104 is fixed, then detector array 114 may be fixed in position parallel to and extending along an axis of a charged particle beam 108 delivered from radiation therapy output 104. In some aspects, detector array 114 may be moved relative to radiation therapy output 104 and/or the patient, so long as the parallel orientation of detector array 114 relative to charged particle beam 108 is maintained.

Detector array 114 is configured to detect magnetic fields generated by one or more particle beams 108 delivered to a patient from radiation therapy output 104. Detector array 114 may be a one-dimensional (1-D) array or a two-dimensional (2-D) array. FIG. 2A depicts a 1-D detector array 114. Detector array 114 may include a plurality of individual detectors 119 arranged in a line along the depth of the planned trajectory of a charged particle beam 108. The vertical direction of detector array 114 shown in FIG. 2A corresponds to the depth of the array along the particle beam trajectory. Detectors 119 of detector array 114 may be spaced approximately one millimeter apart from one another, although, in some embodiments, detectors 119 may be spaced less than one millimeter apart or may be spaced more than one millimeter apart, for example, one centimeter or more apart from one another. The spacing between detectors 119 may be constant or may vary along the array. For example, in some embodiments, there may be a higher concentration of detectors 119 located at a central region of detector array 114 or in a region of detector array 114 that corresponds to an average depth of charged particle beam delivery. In such embodiments, the decrease in spacing between detectors 119 along a portion of detector array 114 near where charged particle beams 108 are more likely to terminate may increase the accuracy of detector array 114 in a cost-efficient manner by increasing the number of detectors in the region of detector array most likely to detect termination of the charged particle beam.

Figure 2B:
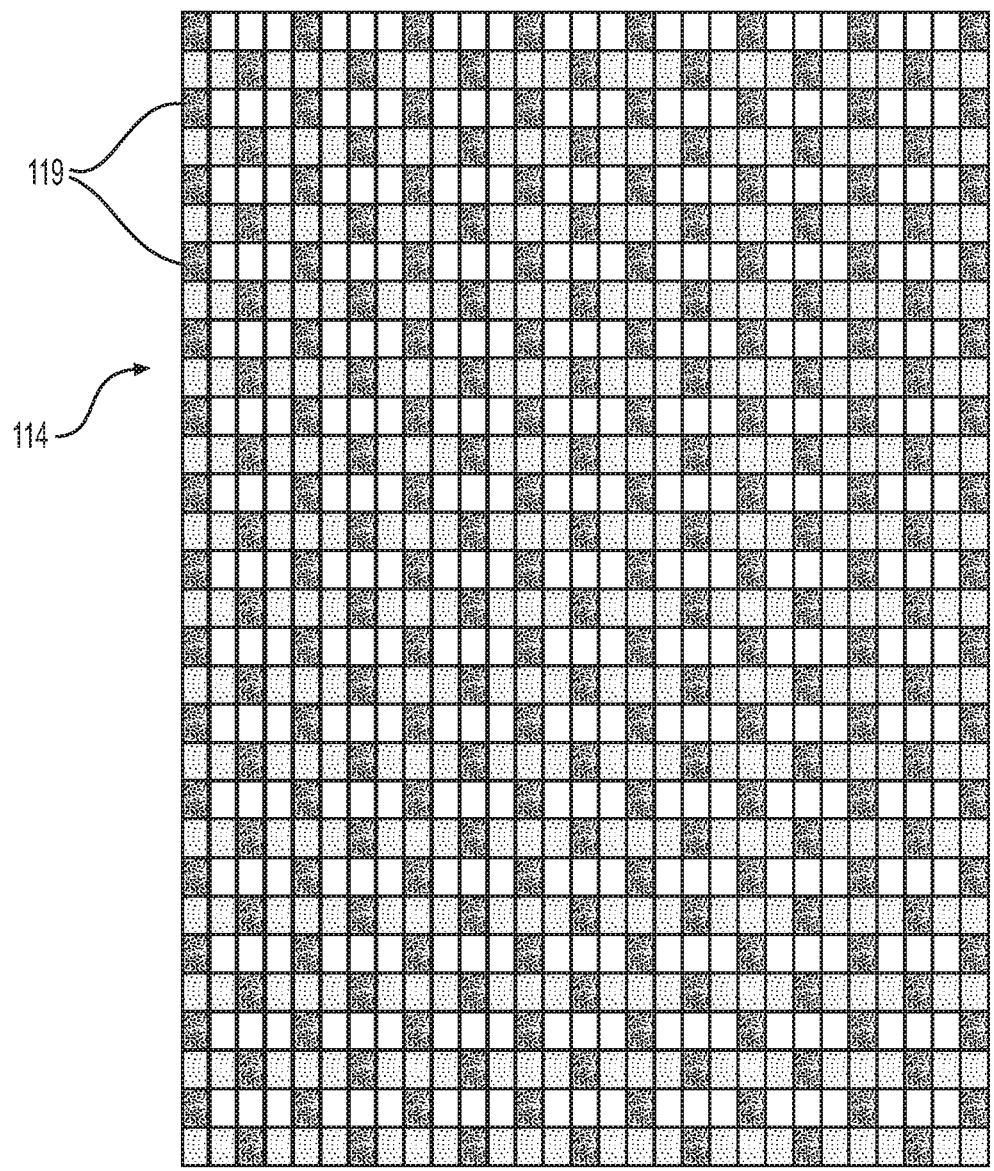
FIG. 2B schematically depicts a detector array, according to various embodiments of the present disclosure.

FIG. 2B depicts a 2-D detector array 114. Detector array 114 may include a plurality of detectors 119 arranged along the depth of the planned trajectory of a charged particle beam, as well as along the width of the planned trajectory of the charged particle beam. The vertical direction of detector array 114 shown in FIG. 2B corresponds to the depth of the array along the charged particle beam trajectory. In some embodiments, as in the embodiment depicted in FIG. 2B, there may be a higher density of detectors 119 in the direction of the depth of the charged particle beam, compared to the density of detectors 119 in the direction of the width of the beam. This may increase the accuracy of detector array 114 along the depth of the beam, resulting in a more accurate assessment of the beam end point location. Exemplary spacing between individual detectors 119 may be approximately one millimeter apart from one another, although, in some embodiments, detectors 119 may be spaced less than one millimeter apart or may be spaced more than one millimeter apart, for example, one centimeter apart or more apart from one another. In some embodiments, the spacing of detectors 119 may be different along the depth of the charged particle beam than it is along the width of the beam. For example, detectors 119 may be spaced approximately 1 millimeter to approximately 3 millimeters apart from each other along the depth of the beam, and may be spaced approximately 5 millimeters to approximately 15 millimeters apart from each other along the width of the beam. The spacing between detectors 119 along the depth and/or along the width of detector array 114 may be constant or may vary between detectors. For example, in some embodiments, there may be a higher concentration of detectors 119 located at a central region of detector array 114 or in a region of detector array 114 that corresponds to an average depth of beam delivery. In such embodiments, the decrease in spacing between detectors 119 along a portion of detector array 114 near where charged particle beams 108 are more likely to terminate may increase the accuracy of detector array 114 in a cost-efficient manner.

In some embodiments, individual detectors 119 may be aligned in rows along the depth and/or the width of detector array 114, while in other embodiments, detectors 119 may be interdigitated, as shown in FIG. 2B. The interdigitation of detectors 119 may provide some advantages in terms of signal "sampling" (vis the Nyquist-Shannon sampling theorem). Depending on the inherent spatial variation of the signal being detected, it may be necessary to acquire samples at a sufficient density so that a transition in the magnetic field generated by charged particle beam 108 is not missed. In some aspects, it may be possible to pre-filter the signal to avoid a situation in which there is more variation than detectors 119 of detector array 114 are capable of detecting. Otherwise, the signal generated by beam 108 may be aliased. In this situation, the signal may slowly vary spatially. Interdigitating detectors 119, as shown in FIG. 2B, may allow for using subsets of detector array 114 to improve determination of the lateral position of beam 108, compared to having detectors 119 spaced in rows. Interdigitation may allow detector array 114 to include fewer detectors without significantly compromising accuracy.

In some aspects, detectors 119 may be arranged in an arc along detector array 114. The arc may follow the trajectories of pencil beams that are guided vertically and horizontally, but with a constant, previously identified virtual source axis distance of beam 108. For example, the virtual source axis distance may be particular for a given radiotherapy system 102, e.g., if the vendor were to choose to have a constant virtual source axis distance. An arc configuration of detectors 119 may maximize the alignment of a 1-D detector array 114 along the beam arc to manipulate the signal to more closely follow the model and to optimize the signal detection.

In some embodiments, a second, e.g., smaller, detector array (not shown) may be positioned perpendicular to surface 116, in addition to, or instead of, one or more arrays mounted parallel to surface 116. For example, the smaller, perpendicular detector array may be used for head or neck radiotherapy or for prostate radiotherapy. In some aspects, the orthogonal arrangement of a smaller detector array 114 in combination with one or more parallel detector arrays 114 may provide 3-D positioning information when using 1-D detector arrays. One detector array 114 (e.g., the parallel detector array) may provide x- and y-axis information, and a second one detector array (e.g., the perpendicular detector array) may provide y- and z-axis information. In this manner, multiple detector arrays 114 may be used to monitor particle beams 108.

The arrangements of detectors in FIGS. 2A and 2B may be optimized for detection of the depth and/or range of charged particle beams. The magnetic fields generated by charged particle beams 108 are vector fields, having x, y, and z components. Detector array 114 comprises one or more individual detectors, as shown in FIGS. 2A and 2B, to detect portions of the magnetic field. In some embodiments, individual detectors 119 may each have a planar surface and may measure only the component of the magnetic field that is perpendicular to the surface of the detector. For an axial charged particle beam 108, a detector placed above or below charged particle beam 108 may detect a maximum signal by having the planar surfaces of individual detectors 119 oriented perpendicular to detector array 114. In an exemplary embodiment, a planar detector array 114 may be oriented in a plane parallel to charged particle beam 108 so that detector array 114 extends above charged particle beam 108 in the direction of charged particle beam 108. In some embodiments, detector array 114 may include one or more vector magnetometers, which may be able to measure all three components (x, y, and z) of the magnetic field generated by a charged particle beam 108. In some aspects, detector arrays 114 including vector magnetometers may require a greater number of individual detectors 119 than detector arrays 114 including other types of detectors 119.

In some embodiments, detector array 114 may be oriented parallel to particle beam 108, but individual detectors 119 may be angled relative to the magnetic field and at an angle to an axis of detector array 114 extending parallel to charged particle beam 108. For example, a detector array 114 may optimize the measurement of the axial beam by having the planar surfaces of the individual detectors oriented to an approximate expected distance relative to the beam axis.

In some aspects, it may be possible to cross-connect adjacent detectors 119 to measure the difference in detected magnetic field values between the adjacent detectors 119. For example, this may allow for signal de-noising, because external fields that are detected by both detectors 119 and whose spatial variation is similar to one another may be rejected as signal noise. This may optimize detector array 114 for the field of interest and/or may decrease the amount of spurious magnetic fields (i.e., noise) detected by detector array 114.

Figure 2C:
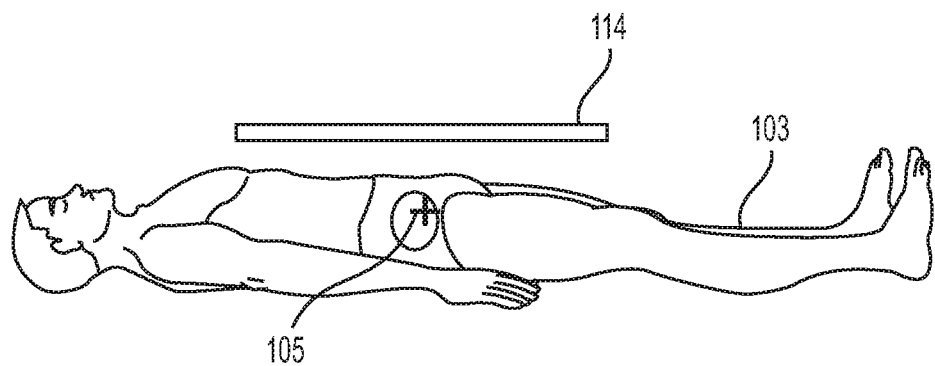
FIG. 2C depicts an exemplary positioning of a detector array relative to a patient, according to various embodiments of the present disclosure.
Figure 2D:
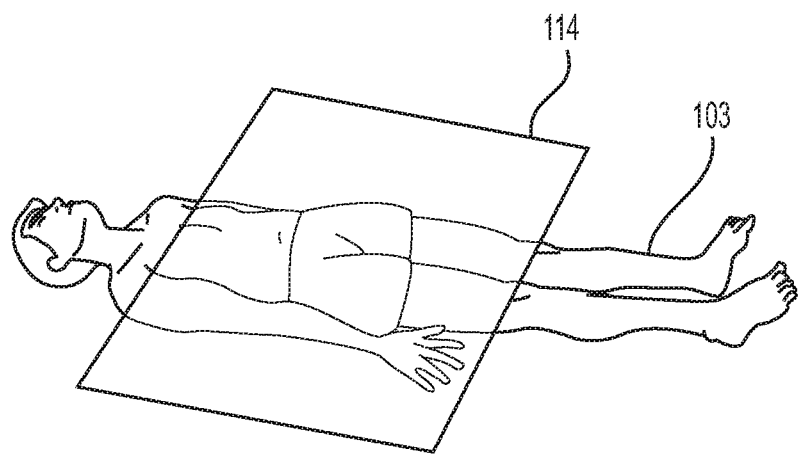
FIG. 2D depicts an exemplary positioning of a detector array relative to a patient, according to various embodiments of the present disclosure.

FIGS. 2C and 2D depict the orientation of detector array 114 relative to a patient 103 placed in a supine position. The plus sign 105 (FIG. 2C) indicates the entry point of a charged particle beam delivered by radiotherapy system 102 into patient 103. Detector array 114 is positioned above patient 103 so that the depth of detector array 114 extends parallel to the trajectory of the charged particle beam as it passes through patient 103. Detector array 114 may be located as close to patient 103 and charged particle beam 108 as possible, while still allowing for the safety of the patient. For example, detector array 114 may be positioned several millimeters or several centimeters away from patient 103. In some aspects, detector array 114 may be located a distance of less than 40 centimeters away from the patient (e.g., 10 centimeters or 20 centimeters), or less than 60 centimeters away from the patient. The specific distance detector array 114 may be away from patient 103 may depend on one or more factors, including, e.g., the type of the detectors 119 used, the signal-to-noise ratio of detector array 114, the location of charged particle beam 108 within the body, the type of charged particle beam 108 used, the size of the patient, and/or the algorithm(s) used for identifying the stopping point/Bragg peak of charged particle beam 108. In some embodiments, detector array 114 may be separated from patient 114 by a barrier. For example, detector array 114 may be separated from patient 103 by a barrier made of, e.g., plastic, fiberglass, or glass. A barrier may extend between patient 103 and detector array 114, or detector array 114 may be partially or completely enclosed in a housing. In some aspects, the barrier or housing may be placed in contact with patient 103, so that the thickness of the barrier or housing separates detector array 114 from patient 103.

In some embodiments, detector array 114 may be positioned below patient 103, instead of, or in addition to, detector array 114 positioned above patient 103. If two detector arrays 114 are used, the magnetic fields on either side of the patient may be detected, and information detected by each detector array 114 may be compared to assess accuracy of the detected magnetic fields. For example, in some embodiments, the use of two separate arrays may facilitate removal of signal noise from the detector readings.

In terms of generating 3-D data, having detector arrays 114 located both above and below the patient may produce a different distribution of magnetic field, with each detector array 114 providing an approximation of the distance of particle beam 108 from each detector array 114, and, in combination, may provide a more accurate estimate of beam end point location. While a single detector array 114 may provide x and y information (coordinate frame of the detector), using two detector arrays 114 in combination may also provide improved determination of z information, making it possible to acquire 3-D information of the trajectory of beam 108 with two detector arrays 114. Having a full vector magnetometer detection system may also provide 3-D information, because the relative intensity of the components will vary based on the distance from beam 108 detector array 114 is in a readily modeled fashion.

In some embodiments, radiotherapy system 102 may include two detector arrays 114, but only the detector array closest to the charged particle beam may be used. For example, if the target region of the patient is located closer to the front of patient 103 (assuming the supine position of FIGS. 2C and 2D), then the detector array above patient 103 may be used. If the target region of the patient is located closer to the back of patient 103 (again assuming the supine position of FIGS. 2C and 2D), then a detector array below patient 103 (not shown) may be used.

Figure 3:
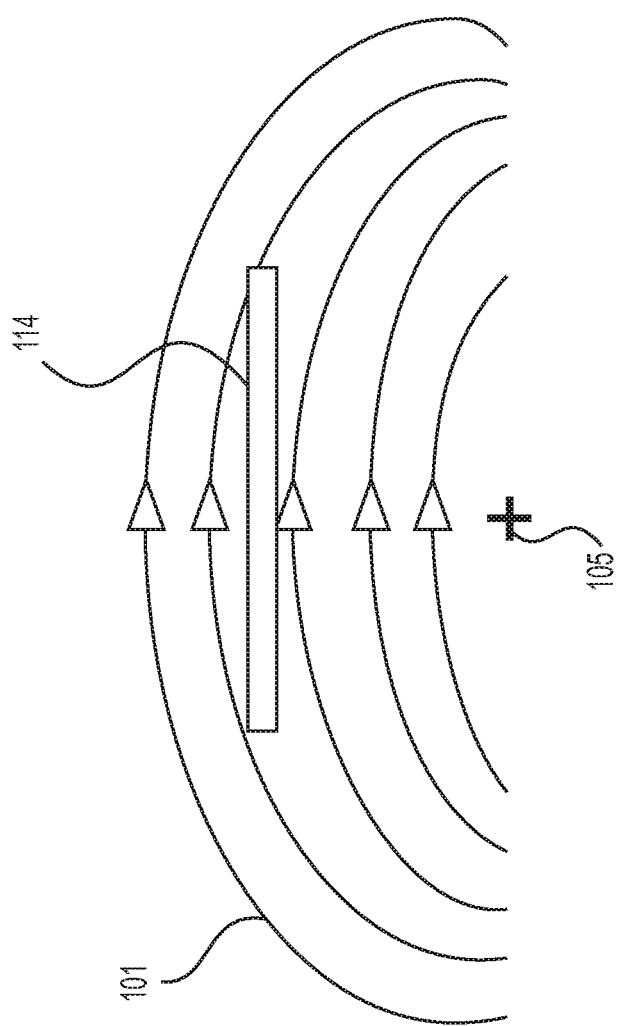
FIG. 3 schematically depicts a magnetic field relative to an exemplary detector array, in accordance with embodiments of the present disclosure.

Each charged particle beam generates a magnetic field. Each detector 119 of detector array 114 may be configured to detect the magnetic field or magnetic field gradient generated by each charged particle beam. Accordingly, detectors 119 may be configured to detect currents generated by a charged particle beam, e.g., nanoampere currents. FIG. 3 depicts detector array 114 positioned relative to magnetic field 101 generated by a charged particle beam entering the body at the location of plus sign 105. As a charged particle beam passes through the body of patient 103, the beam may dissipate, and the current may lessen. Each detector 119 located above (and/or below) the beam detects whether or not the beam extends to the location of that individual detector in the array by detecting the presence or absence of a magnetic current. Accordingly, if the magnetic field of a charged particle beam is detected by one detector 119 but is not detected by a neighboring detector 119 of detector array 114, then the charged particle beam may have terminated between the neighboring detectors. Or, if the magnetic field generated by a charged particle beam is detected by one detector 119, but less of the magnetic field is detected by the neighboring detector, then the charged particle beam may have terminated (i.e., the Bragg peak may have occurred) between the neighboring detectors.

The measured magnetic field data may provide a set of data that can be used to determine the end points of charged particle beams using detector array 114. Algorithms used to determine the range and/or depth of the charged particle beams based on the detector measurements may assume a line segment of current along the charged particle beam in order to determine the end point of that line segment. In some aspects, treatment planning information regarding prescribed magnetic field values for the location, direction, and/or expected range of the charged particle beam may also be incorporated into such calculations in order to assess the measurements from detector array 114.

Figure 4:
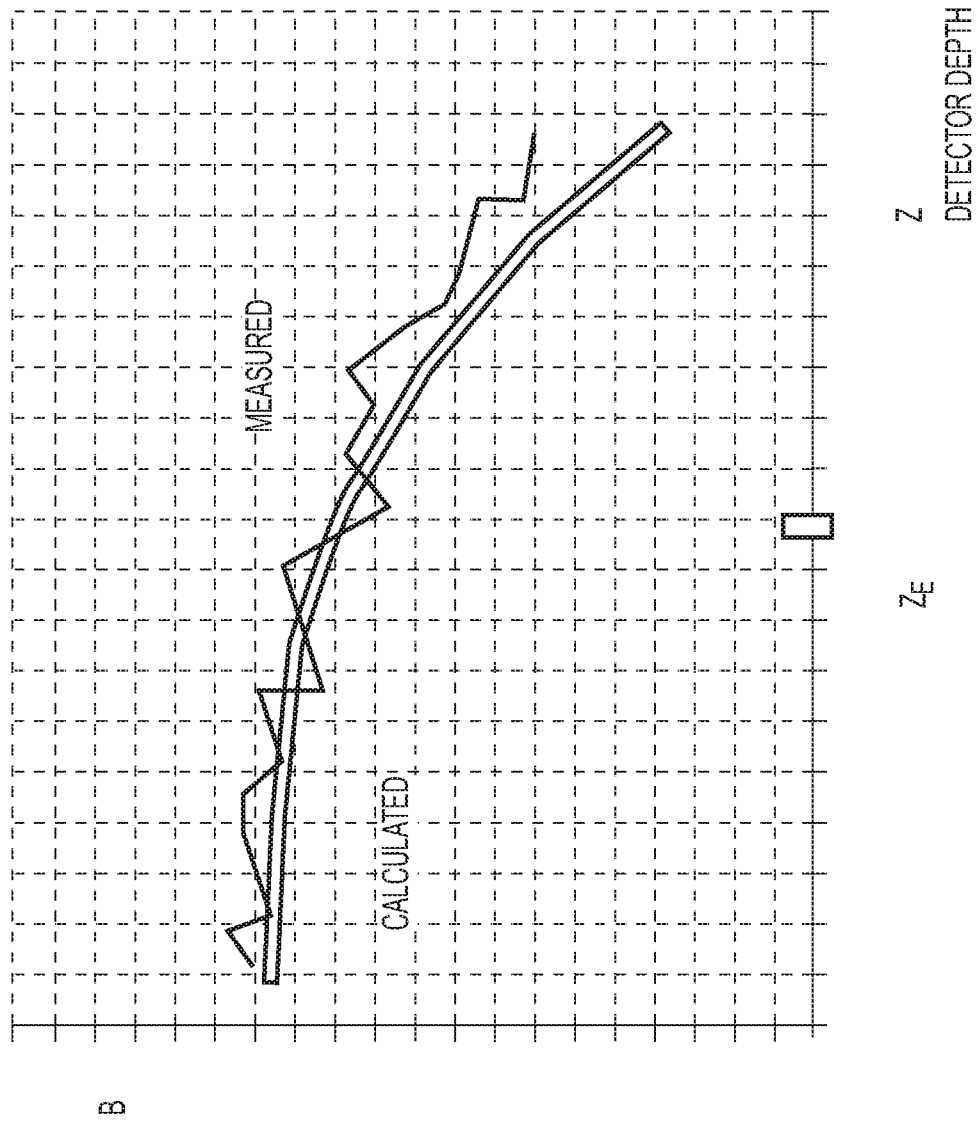
FIG. 4 graphically depicts an exemplary trajectory of a charged particle beam as it moves along a depth of an exemplary detector array, in accordance with embodiments of the present disclosure.

FIG. 4 graphically depicts the fall off of the charged particle beam as it extends further into the body. The z-axis depicts the depth along a detector array 114, and the y-axis depicts the magnetic field (B). At point $Z_E$, the magnetic field generated by the charged particle beam begins to drop off, and the magnetic field may not be detected by a detector 119 located after position $Z_E$. A detector 119 located just prior to that position, however, would detect the magnetic field generated by the charged particle beam, and thus detector array 114 would detect that the beam terminated between the two neighboring detectors. In some aspects, a detector 119 located after position $Z_E$ may detect less of a magnetic field than a detector immediately prior to position $Z_E$, which may indicate that the charged particle beam 'terminated' between the two detectors, in that the Bragg peak occurred before the detector that detected less of a magnetic field. The calculated beam trajectory estimated during treatment planning (shown in bold) predicts a beam end point at point $Z_E$, where the beam falls off. The magnetic field measurements detected by detector array 114 show an actual, in vivo beam end point located at approximately the same location and following a trajectory similar to the estimated beam trajectory, although not identical. The differences between the actual magnetic field measurements and the estimated trajectory may be due, at least in part, to variations in the stopping power of the anatomy through which the beam passed.

The accuracy of detector array 114 may therefore depend at least in part on the spacing of individual detectors 119 within the array. A detector array 114 having more closely spaced detectors 119 may provide more specific information as to the location of the beam termination, while an array with detectors 119 spaced further apart may provide a more general reading of where the beam may have terminated. In some embodiments, detectors 119 may be spaced approximately one millimeter apart from one another, although, in some embodiments, detectors 119 may be spaced less than one millimeter apart or may be spaced more than one millimeter apart, for example, one centimeter apart or more. The more detectors 119 included in detector array 114, the more accurate detector array 114 may be. Ultimately, however, the spacing and number of detectors 119 included in detector array 114 may be practically constrained by the cost and/or size of the detectors. The number of detectors 119 in detector array 114 may range from 10 to 100 detectors, e.g., 12 detectors, although some linear arrays may have less than 10 or more than 20 detectors.

If a 1-D detector array is used, then detector array 114 may be able to determine the end point of a charged particle beam. If a 2-D detector array is used, then detector array 114 may be able to determine both the location of the end point of a charged particle beam, as well as the direction in which the charged particle beam is pointing. A 1-D detector array 114 may require careful positioning along the axis of charged particle beam 108 to provide optimal discrimination capability. This is because charged particle beams 108 that are positioned off angle from detector array 114 may generate blurrier signals. A 2-D detector array 114 may allow detectors 119 to be positioned close to the beam, resulting in improved discrimination and a sharper signal.

Detector array 114 may include any suitable detectors 119 or combination of detectors 119. For example, detector array 114 may include one or more superconducting quantum interference devices (SQUID), laser-pumped detectors (e.g., rubidium laser-pumped detectors), or magnetometers, or other suitable detectors or combinations thereof. In some embodiments, larger detectors may be used, which may be more sensitive to the magnetic fields generated by charged particle beams.

One or more forms of magnetic field gradient measurement techniques may be used in conjunction with detector array 114 to remove spurious magnetic field influence, which may come, e.g., from the Earth itself and/or from nearby equipment that may generate a magnetic field. In some embodiments, it may be possible to gate the readings from detector array 114 using information regarding the timing of the initiation and termination of the particle beam delivery. For example, by knowing when the charged particle beam is being delivered and when it is not, it may be possible to remove extraneous noise in the detector signals. Detector array 114 may be used to detect the magnetic field prior to initiation of the particle beam to acquire a baseline of background noise, and then the detector array may be used to detect the magnetic field during beam delivery. Signals detected both when the beam is 'on' and when it is 'off' may be removed, since they are not being generated by the beam.

In some aspects, magnetic field shielding may be used in conjunction with detector array 114 to reduce signal noise picked up by detector array 114. For example, rooms may be shielded from external magnetic fields using, e.g., a nickel—iron magnetic alloy (like Mumetal®), aluminum, or other suitable metals or alloys thereof. For a gantry-based radiotherapy system 102, shielding may be included on or may encompass gantry 106. For a fixed beam radiotherapy system, a shielded room may be used that has a small opening through which charged particle beam 108 may be delivered. For example, a portion of the radiotherapy system that delivers a charged particle beam 108 may be protruded through or aligned with the opening in the room shielding (e.g., a snout, if one is used). Additionally or alternatively, magnetic field shielding may be positioned to surround a magnetic field used to steer a pencil beam, which may occur outside of a treatment room or within a snout. This magnetic field shielding might be, e.g., a soft core iron or other suitable material.

The planned trajectory of the particle beam may be used in conjunction with detector array 114 for determining charged particle beam end point locations. For example, knowing the planned trajectory of the beam narrow the solution space in which detectors 119 of detector array 114 must search, or may be used to adjust the orientation of individual detectors 119, and/or may narrow the range of detectors 119. For example, in some embodiments, individual detectors 119 of detector array may be moved manually or automatically to optimize detection of the magnetic field, or a portion of the magnetic field, generated by charged particle beam 108.

Prior to treatment, the trajectory of the charged particle beam may be calibrated, e.g., based on measurements using dose or particle detectors in water phantoms or in free air. For example, to calibrate the charged particle beam, a length of insulated wire extending in the expected direction of the charged particle beam may be used to simulate a charged particle beam. The length of wire may be connected to a source of current (for example, a battery with a resistor) to control the magnitude of the current, which may be adjusted to match the expected current generated by a charged particle beam. The wire may also be connected to a switch (for example, a semiconductor or transistor) to control the current flow, with a right angle to the beam and the plane of the detector array continuing some distance (e.g., several centimeters or up to 100 cm) and ending on a conducting volume, which returns to the source of the current. The corner of the length of the wire may be placed at specific locations along the expected path of the charged particle beam (e.g., along the isocentric axis of the beam, as well as along paths expected for x and y grid locations typically used by the radiotherapy device for spot scanning). The detector array may be used to capture data for each specific location, and the fall off of the transverse magnetic field along the direction of the wire (simulating the charged particle beam) may be measured.

In some embodiments, calibration may include the use of a half-line source. A half-line source may be emulated using a water tank containing a conductive solution (e.g., saline solution) with an insulated wire cut at the tip to act as an anode and a large/wide cathode placed in the tank at a distance from the detector array. The detector array may be used to capture data, and the fall off of the transverse magnetic field along the direction of the wire (again simulating the charged particle beam) may be measured. It is also possible to switch the anode and the cathode, but doing so would switch the direction of the magnetic field, which would need to be accounted for mathematically for future correlation purposes.

Based on the calibrated beam trajectory, the position of the patient, and the position of the particle beam delivery device, it may be possible to pre-calculate the expected magnetic field distribution for a variety of beam end points expected to occur during radiotherapy. Each beam end point—Bragg peak location—has an expected depth within the patient, which may be calculated based on patient models formed during treatment planning. The magnetic field measurements may be used to determine a best-fit estimation of the actual depth or end point of each charged particle beam during radiotherapy. During radiotherapy, the actual, measured magnetic field values may then be compared to the expected values to identify the best match using mathematical techniques like cross-correlation. A least squares fit between the measured curve and the calibration curves may be used. A curve may be fitted to the fall off of the magnetic field, and a correlation may be constructed between the sets of curves with the positions of the corner of the length of wire used during calibration. Correlation of the measured curve in-vivo may be made with the calibrated curves to determine the end point of the beam (which may be equivalent to the position of the corner of the wire). The calibration curves may have known end points, regardless of what material or set of inhomogeneous materials were in the path of the delivered beam.

The expected magnetic field generated by the charged particle beam may be calculated using the Biot-Savart law for finite current segments during pre-planning. The Biot-Savart law is the fundamental formula for determining the magnetic field generated by an electric current—like that produced by a charged particle beam—for a point charge. In the case of a point charged particle q moving at a constant velocity v, Maxwell's equations give the following expression for the electric field and magnetic field:

$$E = \frac{q}{4\pi\epsilon_0} \frac{1 - v^2/c^2}{(1 - v^2\sin^2\theta/c^2)^{3/2}} \frac{\hat{r}'}{|r'|^2}$$

$$B = \frac{1}{c^2} v \times E$$

The algorithm for the forward calculation involves following an individual proton—or other charged particle—through its entrance into the patient, discretizing it's travel using the known stopping powers for the body tissues and materials through which the proton would pass along its trajectory, then determining the velocity of the proton (accounting for it being relativistic), and summing up the contributions along the path to where the proton "stops." The alternative way of looking at it is to say that there is a steady beam of protons coming in, and along the path that the protons take, they are divided up into groups that have the same average velocity, and the contribution from each group may be summed. Each group is bunched in increments of particle energy. For example, typical spot scanning beams are specified to a precision of 0.1 MeV prior to any degradation by a beam line device, such as a range shifter. Initial modeling has been with energy increments of approximately 1 MeV to approximately 250 MeV. For a given increment of energy, with a given starting energy for that increment, there is a specific distance that the particle will travel, which is the difference in the projected range between the initial energy for that segment and the initial energy reduced by the increment of energy. That increment has an average position, nominally the midpoint of the segment. A complete model may include the distribution of the one or more groups of protons emitted from the accelerator, but the initial approximation is a uniform distribution along the length of the beam at entrance, with the density increasing in each segment as the velocity decreases. The density increase and velocity decrease occur as a steady stream of evenly spaced protons go through successive decreases in speed and become more tightly, but still evenly, spaced within a given speed. Each group is summed up based on its contribution to the magnetic field at a particular detector, having a distance to the midpoint of the segment.

Figure 5:
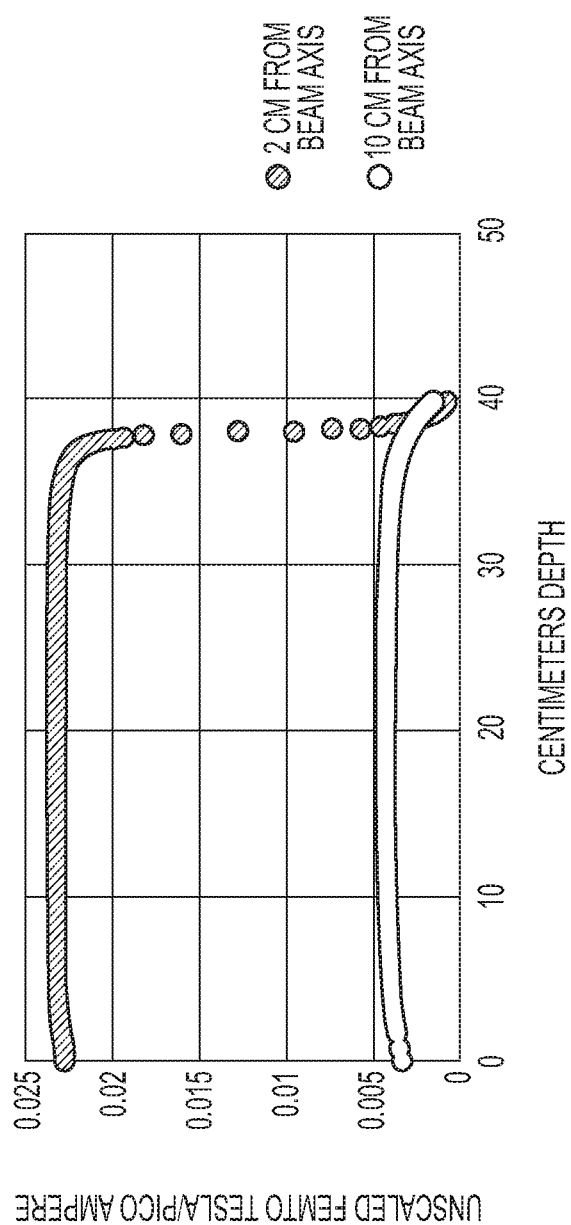
FIG. 5 graphically depicts the outcomes of various magnetic field calculations for a charged particle beam, in accordance with embodiments of the present disclosure.

FIG. 5 graphically depicts the resulting beam trajectory paths and end points for a 250 MeV proton beam travelling into a water phantom. In FIG. 5, the proton beam enters the phantom or the body of the patient at a distance of approximately 40 centimeters from the end point of the beam. In the exemplary embodiment in which the curves were calculated, one of the proton beam paths was delivered approximately 2 centimeters lateral and the other was delivered approximately 10 centimeters lateral from a simulated 1-D detector array with negligible vertical separation of the charged particle beam from the detector array. Similar results may be obtained for equivalent distances to the detector array for combinations of lateral and vertical distances to a 2-D detector array. The simulated measurements show that the magnetic field falls off at the location of the Bragg peak (based on information from the (USA) National Institute of Standards and Technology). Accordingly, by looking at FIG. 5, it is possible to determine where the end point of the charged particle beam is located. A sharp fall off indicates the end of the charged particle beam. A line can be fit to the fall off, and where that line crosses the flatter part of the curve (also line fit . . . so basically, the intersection of two line fits) can be observed. For charged particle beams that are further from the detector array (e.g., 10 centimeters or further), the fall off may not be as sharp, and the region of the fall off that corresponds to the Bragg peak of the particle beam may be determined by fitting two curves that were simulated at particular depths or that were calibrated at particular depths.

For a 2-D detector array, the projection of the trajectory of the charged particle beam path onto the detector array may be measurable based on the ridge of maximum overall strength of the magnetic field generated by the charged particle beam and the vector change (sign change) perpendicular to the plane of the detector array on either side of the trajectory. Using an orthogonal pair of detector arrays (e.g. one posterior to the patient's head and the other superior to the patient's head) provides two projections of trajectories. One detector array may provide xy data and the other detector array may provide yz data so that definitive information on the 3-D trajectory of the charged particle beam path may be determined based on the combination of data from the two arrays. By being able to determine the 3-D trajectory of the charged particle beam, it may be easier to determine the stopping powers of the portions of the body though which the charged particle beam passed. This is because knowing the 3-D trajectory allows for determination of not only where the charged particle beam stopped, but also what path (and what it went through) to get to that stopping point.

The measured and calculated location of the beam end points may be used for one or more purposes. For example, the beam end points may be used to update the positions of the expected end point locations in a radiation plan—e.g., by conversion of the estimated initial energy of the end point in a DICOM RT Ion Plan, or by more direct manipulation of the information within a treatment planning system—to provide a more accurate calculation of the dose distribution for the treatment fraction that was delivered and measured.

In some aspects, the beam end points may be used to update the mapping of the patient imaging values to particle stopping powers. The use of the difference of measured depths between charged particle beams having the same trajectory and incrementally different initial energies may provide a way of estimating the stopping power of a portion of tissue between those two measured depths, and may be computed for each trajectory and each incremental energy difference.

For example, if a beam has an initial energy of 200 MeV, and it stops at a depth of 38 cm, then it can be deduced that the beam did not travel through an object that has a density equivalent to that of water. If the beam had traveled through water, or a substance with an equivalent density to that of water, then a 200 MeV beam would have stopped at a depth of approximately 25.9 cm. Accordingly, based on knowledge of the actual beam depth and the stopping power of water, it can be determined that the beam traveled though at least some tissue that had a density less than that of water. As a result, if a beam that has an initial energy of 190 MeV is then passed through the same trajectory as the 200 MeV beam, it can be inferred that the 190 MeV beam will stop short of 38 cm. If the whole path were through water, then a 190 MeV beam would stop at a depth of 23.7 cm. So, the expected difference in water would be 2.2 cm. Both the 190 MeV beam and the 200 MeV travelled through the same set of material, with the exception of the very end of the 200 MeV beam, which is where the higher energy beam would still have some energy remaining and, as a result, would travel slightly further. Beginning with approximating the average density up to the end point of the 190 MeV beam, it is possible to estimate how much energy would be left in the 200 MeV beam at the end point of the 190 MeV beam. Based on how far that additional energy allowed the beam to travel (the measurement of the difference in ranges), it is then possible to approximate the density of the last portion of the 200 MeV beam by scaling, or fully modeling, the distance a beam of the remaining energy would travel. If the difference in measured distance was 4.4 cm, to first approximation, the density of the last 4.4 cm can be calculated as: (2.2 cm/4.4 cm)=0.5 (grams/cc). This calculation may, however, be sensitive to noise and/or uncertainty in the measurements, but with a large set of differences in depths generated by a plurality of beams traveling along the same trajectories, the densities of the tissues through which the beams traveled can be modeled, assuming that there is high confidence regarding the entrance energy of the beam, until the model aligns with the data.

In some aspects, the beam end points may be used to compare the end point locations estimated by the treatment plan against an acceptable tolerance threshold to determine whether the treatment being delivered is acceptably accurate, if the plan should be modified, or if a new plan should be created. If the actual, measured charged particle beam end point locations and the dose delivered, as determined using detector array 114, fall outside of an acceptable tolerance threshold, then the treatment plan may be modified and/or stopped and/or a new plan may be created.

For example, a treatment planning system may be configured to accept information regarding the magnetic field localization of the charged particle beam end point detected by detector array 114. The treatment planning system may combine the information detected by detector array 114 with patient information gathered during the treatment planning process. Exemplary patient information may include, e.g., medical imaging, information regarding the geometry, size, and/or location of tissue and/or the target region within the patient's body, and the intended trajectories and energies of the particle beams to be delivered to the patient. If the actual beam end point location detected by detector array 114 is within an acceptable threshold—e.g., it generally matches the intended end point location of the charged particle beam assessed during treatment planning, within an acceptable standard deviation—then the current treatment session may be allowed to continue. If the actual beam end point location detected by detector array 114 is outside of an acceptable threshold, then the current treatment session may be aborted. In some embodiments, rather than aborting the current treatment, the current treatment may be modified (e.g., the speed and/or intensity of the charged particle beams being delivered by radiotherapy system 102 may be modified).

For example, a treatment plan and feedback system may be configured so that if the detected charged particle beam measurements fall outside of a given threshold, then the current treatment may be modified in real time. In some aspects, there may be multiple thresholds. For example, if the detected charged particle beam measurements fall outside of a first threshold, then the current treatment may be modified, but if the detected charged particle beam measurements fall outside of a second threshold, greater than the first threshold, then the current treatment may be aborted. In some embodiments, the current treatment session may not be modified (only continued or aborted), but subsequent treatment sessions may be modified based on the measurements detected by detector array 114. In some aspects, if there is deviation within the threshold or deviation outside of a threshold, one or more subsequent treatment sessions may be modified to compensate for that deviation.

Furthermore, the treatment planning system may be configured to generate a pre-calculated map of magnetic field values for each beam end point with position values relative to the medical imaging and/or treatment isocenter. Measurements detected by detector array 114 may be compared to this pre-calculated map. In some embodiments, the map may be modified based on the actual, measured magnetic field readings detected by detector array 114.

In some embodiments, radiotherapy system 102 may include one or more monitors for graphical image representations of the magnetic field detected by detector array 114. The magnetic field information may be displayed as a chart, graph, pictorial image, and/or text. In some aspects, the detected magnetic field information may be displayed relative to the expected measurement values and/or may be overlaid with medical imaging showing the patient's body, including, e.g., the target region and/or surrounding structures.

Figure 6:
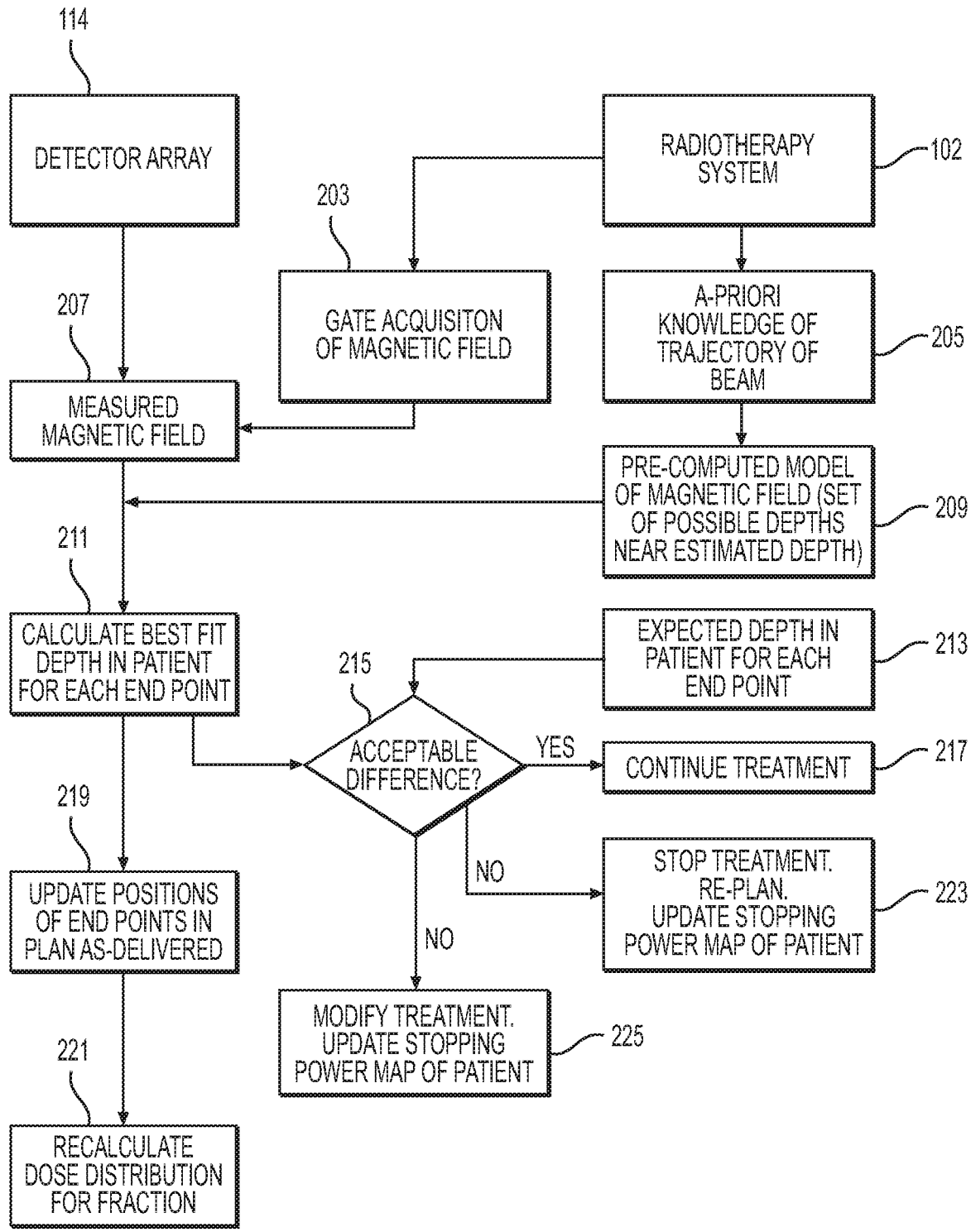
FIG. 6 is a flow chart depicting an exemplary method, in accordance with embodiments of the present disclosure.

FIG. 6 depicts a flow chart of an exemplary method of determining the end point of a charged particle beam and using the determined end point location to inform radiotherapy using detector array 114 and radiotherapy system 102. In some aspects, radiotherapy system 102 may be configured to deliver a pencil beam of protons and may include a beam scanning control. Radiotherapy system 102 may be used to gate acquisition of the magnetic field generated by the charged particle beam (203), for example, by detecting the presence of signals measured by detector array 114 when the beam is 'on' versus when the beam is 'off' to remove background noise. Radiotherapy system 102, or a larger system of which radiotherapy system 102 is a part of, may store a-priory knowledge of the intended trajectory of the beam (205) based on treatment planning. A pre-computed model of the magnetic field may comprise a set of possible beam depths within the body near the predicted depth (209). Detector array 114 may measure the magnetic field generated during charged particle beam delivery (207), and the measured signals may be compared with gating information to remove noise. The pre-computed model of the expected magnetic field may be compared with magnetic field measurements taken by detector array 114 to assess best fit depths within the patient for the end point location for each charged particle beam (211). For example, a curve-fitting calibration may be performed to determine an estimate of where within a patient each charged particle beam delivered during treatment actually stopped. The record of the plan as-delivered may be updated to reflect the measured best-fit depth for each end point (219). Alternatively or additionally, the treatment record may be updated to reflect the measured best-fit depth for each end point (211). Based on the best-fit information and/or the updates to the treatment record and/or plan as-delivered, the dose distribution for the treatment fraction may be recalculated (221). This may also necessitate the recalculation of the doses to be delivered during subsequent fractions.

The best fit depth (211) calculated based on the readings from detector array 114 may be compared to the expected depth in the patient at each end point (213), estimated during the preplanning, to determine whether there is a difference between the expected depth of the beam end point and the best fit depth of the beam end point actually delivered, and, if there is a difference, to determine whether this difference falls within an acceptable threshold (215). If the difference is acceptable (217), then radiotherapy system 102 may continue to administer the radiotherapy treatment (i.e., the charged particle beams). If the difference falls outside of an acceptable threshold, then the treatment may be stopped. The pre-plan may be updated or altered to reflect this difference (223). The stopping power map of surrounding and/or intervening tissues within the patient may also be modified according to the actual depth of the charged particle beams detected by detector array 114. This may also result in the modification of subsequent treatment sessions. In some embodiments, if the difference falls outside of an acceptable threshold, then the current treatment may be modified in real time (225) rather than aborted. In such embodiments, the preplan may also be modified, and the stopping power map of surrounding and/or intervening tissues within the patient may be modified according to the actual depth of the charged particle beams detected by detector array 114. This may result in the modification of the present treatment session and/or subsequent treatment sessions. The pre-plan may be updated or altered to reflect this difference (223).

In the method of FIG. 6 and other methods described herein, updating the treatment record, the plan as-delivered, and/or the stopping power map may improve function of radiotherapy system 102 for future treatment fractions for that patient, because the updates based on information measured by detector array 114 may improve the accuracy of future estimates and calculations of beam energies and intensities to achieve the desired dose delivered and delivery location.

Generally, a mismatch between the expected beam end point location and the actual beam end point location may occur for one of at least three reasons. First, incorrect stopping powers may be used during treatment planning. For example, an inaccurate model may be used to start with, and/or the patient morphology may have changed, e.g., due to weight loss. The second common reason for a mismatch may occur when the patient is not accurately positioned, and the administered beam travels through a different part of the patient's body than expected. A third reason for mismatch may occur due to patient movement, e.g., caused by breathing, the filling of the bladder, and/or other shifts in the internal organs.

Exemplary Medical Systems for Performing Processes of the Disclosure

Figure 7:
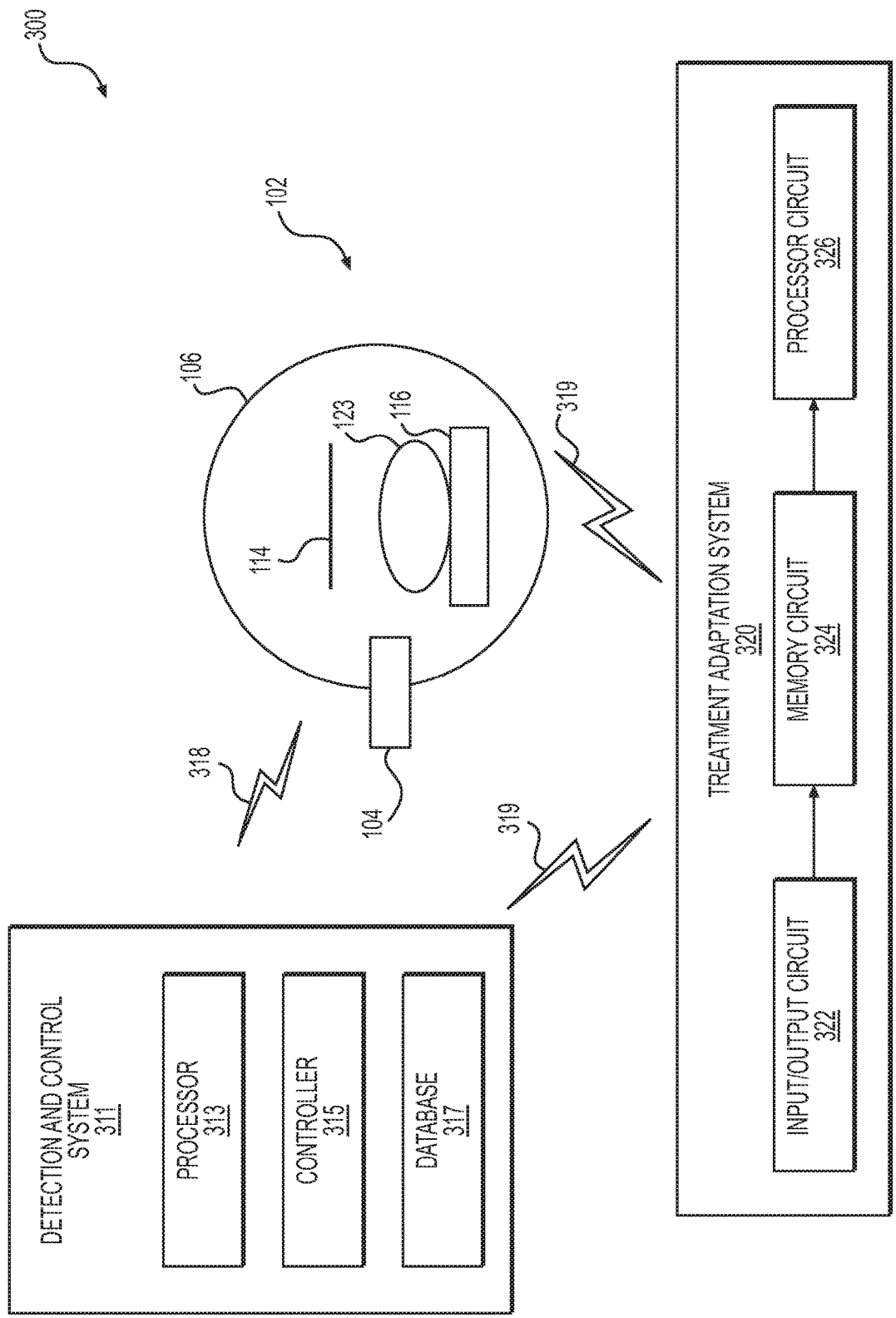
FIG. 7 depicts an exemplary system that may be used to provide real-time charged particle beam end point detection, in accordance with embodiments of the present disclosure.

FIG. 7 depicts an exemplary radiotherapy control system 300 that may be used to provide real-time charged particle beam end point detection and feedback in accordance with various embodiments of the disclosure. Radiotherapy control system 300 may use measurements of the magnetic field detected by detector array 114 obtained in real time to track, control, and/or adapt a radiation therapy treatment plan during the administration of radiotherapy. Radiotherapy control system 300 may include radiotherapy system 102 of FIG. 1. Radiotherapy control system 300 may also include detection and control system 311, which may include processor 313. Processor 313 may be configured to process measurement data received from detector array 114, for example, to perform one or more calculations. In some embodiments, however, radiotherapy system 102 may incorporate a processor and may communicate processed information to detection and control system 311. In some embodiments, a separate processor 313 may be included in radiotherapy control system 300 instead of, or in addition to, a processor integrated into radiotherapy system 102. If a processor is only included in detection and control system 311, then raw measurements from detector array 114 may be communicated to processor 313. Radiotherapy system 102, including detector array 114, may be connected to detection and control system 311, as depicted by lightning bolt 318 (lightning bolt 318 may represent a wired or wireless connection).

Detection and control system 311 may further include a controller 315 in communication with system 102, as depicted by lightning bolt 318 (lightning bolt 318 may represent a wired or wireless connection). Detection and control system 311 may also include a database 317, for example, to store acquired magnetic field measurement information from detector array 114. Measurements received from detector array 114 and/or processed by processor 313 may be used to control and/or adapt treatment of a patient 123. Raw or processed measurement information from detector array 114 may be communicated to controller 315 and database 317 to adapt treatment of patient 123.

Processor 313 (and/or integrated processor within radiotherapy system 102) may acquire and process detected magnetic field information from detector array 114 as one or more charged particle beams are delivered to a patient located within radiotherapy system 102 in order to determine the locations of the end points of each charged particle beam delivered. This information may be compared to the expected locations of the beam end points determined during the treatment planning phase. In some embodiments, the expected location information may be stored in database 317. For example, during a treatment planning phase, a healthcare worker, e.g., physician, nurse, physicist, or technician, may acquire 3-D planning image data prior to treatment of the patient, e.g., via an imaging system separate from and/or integrated within radiotherapy system 102. The 3-D planning image data may be used to determine a precise location of a target region of the patient, e.g., a tumor. A stopping power map may be generated for the patient based on the patient anatomy and/or a model of the predicted magnetic field and possible beam end point depths may be generated. In some embodiments, this planning information may be received in database 317 and/or memory circuit 324. Based on the imaging—which may show the locations of different structures through which the charged particle beams may pass and/or surrounding structures—and based on the stopping power of these structures, the desired end points of the charged particle beams may be pre-calculated. The energy and intensity of the charged particle beams delivered during a treatment session may be determined in order to deliver radiation to the desired locations within the patient's body.

Controller 315 may control one or more aspects of system 300. For example, controller 315 may control portions of radiotherapy system 102. Controller 315 may control the position of the patient (e.g., by controlling movement of surface 116), may control the radiation dosage (e.g., energy and/or intensity) of charged particle beams emitted from radiation therapy output 104, may control or adapt a beam aperture shape or size (e.g., to track the target region), and/or may control the movement and/or positioning of radiation therapy output 104 and/or detector array 114 or the positions of individual detectors 119 relative to patient 123 or relative to each other (e.g., by controlling rotation around gantry 106 or other movements).

System 300 may include a treatment adaptation system (TAS) 320 in communication with detection and control system 311, as represented by lightning bolt 319 (which may represent a wired or wireless connection). TAS 320 may receive data from detection and control system 311 and/or radiotherapy system 102 regarding the magnetic field detected by detector array 114 and/or the position of the charged particle beam end point locations (collectively referred to as detection data). TAS 320 may include an input/output circuit 322 for receiving and transmitting data, a memory circuit 324 for buffering and/or storing data, and a processor circuit 326. Memory circuit 324, which may be any suitably organized data storage facility, may receive magnetic field detection data from detection and control system 311. Memory circuit 324 may receive the detection data via a wireless or wired connection or through conventional data ports and may include circuitry for receiving analog detection data and analog-to-digital conversion circuitry for digitizing the detection data. Memory circuit 324 may provide the detection data to processor circuit 326, which may implement the functionality of the present invention in hardware or software, or a combination of both, on a general- or special-purpose computer. In some embodiments, processor circuit 326 may be a graphical processing unit (GPU).

During operation, radiotherapy system 102 may deliver charged particle beams to a target region of a patient. Detector array 114 may measure the magnetic fields generated by charged particle beams, and the detected information may be processed or otherwise analyzed in order to determine the locations of the end points of the charged particle beams. The detector information collected may be stored in database 317, where other, prior detector information and/or beam end point information may also be stored (for example, the expected beam end point locations based on pre-planning, the beam end point locations from previously emitted charged particle beams delivered in the same treatment session and/or a previous treatment session), and this detector information may be raw or processed. Detector information may be communicated from detection and control system 311 to TAS via input/output circuit 322. The detector information may be stored in memory circuit 324 and communicated to processor circuit 326. Processor circuit 326 may be programmed to carry out a number of different processes and may have software loaded on it to perform different processes, including the calculation of beam end point locations (e.g., using best fit methods or other suitable algorithms and methods), analysis of beam end point locations in current or prior treatments, and/or the comparison of beam end point locations relative to the expected beam end point locations. The processed detector information may be stored in memory circuit 324 and/or may be communicated to detection and control system 311.

Memory circuit 324 may also store information regarding a treatment plan for patient 123, and this information may also be shared with processor circuit 326. Processor circuit 326 may compare real-time, processed detector information from radiotherapy system 102 and/or detection and control system 311 with the predetermined treatment plan for the patient to determine whether the radiotherapy being delivered to patient 123 matches the intended treatment plan for that radiotherapy session. If a variation is detected between the actual delivery of radiotherapy (determined using the detector information generated using detector array 114) and the treatment plan, and that variation falls outside of an allowable threshold of variation, then TAS 320 may communicate this to detection and control system 311. TAS 320 may modify the treatment plan or may stop the radiotherapy treatment altogether, for example, if the variation is beyond a threshold level. This modification or cessation may be communicated to controller 315 of detection and control system 311, which may control a portion of radiotherapy system 102. For example, controller 315 may alter a position of patient 123 via movement of surface 116, may alter the location, shape, energy, and/or intensity of charged particle beams output from radiation therapy output 104 to alter the location of the end points radiation therapy output 104, or may stop the output of charged particle beams from radiation therapy output 104. In this way, detector information may be processed in real time and may be used to control the administration of radiotherapy in real time.

In some embodiments, in addition to or instead of modifying or stopping the current treatment session in real time, future treatment sessions may be modified. For example, if the actual location of one or more charged particle beam end points is different than the expected location, then characteristics (e.g., energy and/or intensity) of subsequent charged particle beams delivered in future treatment sessions may be altered in order to compensate for the deviation and to make sure that the intended dose and intended location of the dose of radiation delivered to the target region is achieved over the course of the treatment sessions.

It should be noted that although a separate detection and control system 311 and a separate TAS 320 are depicted, the systems may be combined into one unit or may be distributed in any suitable manner across multiple separate units. Additionally, one or more units may be located within the treatment administration area or may be located remote from the treatment area. In some embodiments, the processing and data analysis may be integrated into radiotherapy system 102, may be performed within larger detection and radiotherapy system 300, or system 300 and/or system 102 may be connected to a network that is connected to the Internet, and a computer remote from radiotherapy system 102 may perform the processing and analyses described in embodiments of the present disclosure.

Figure 8:
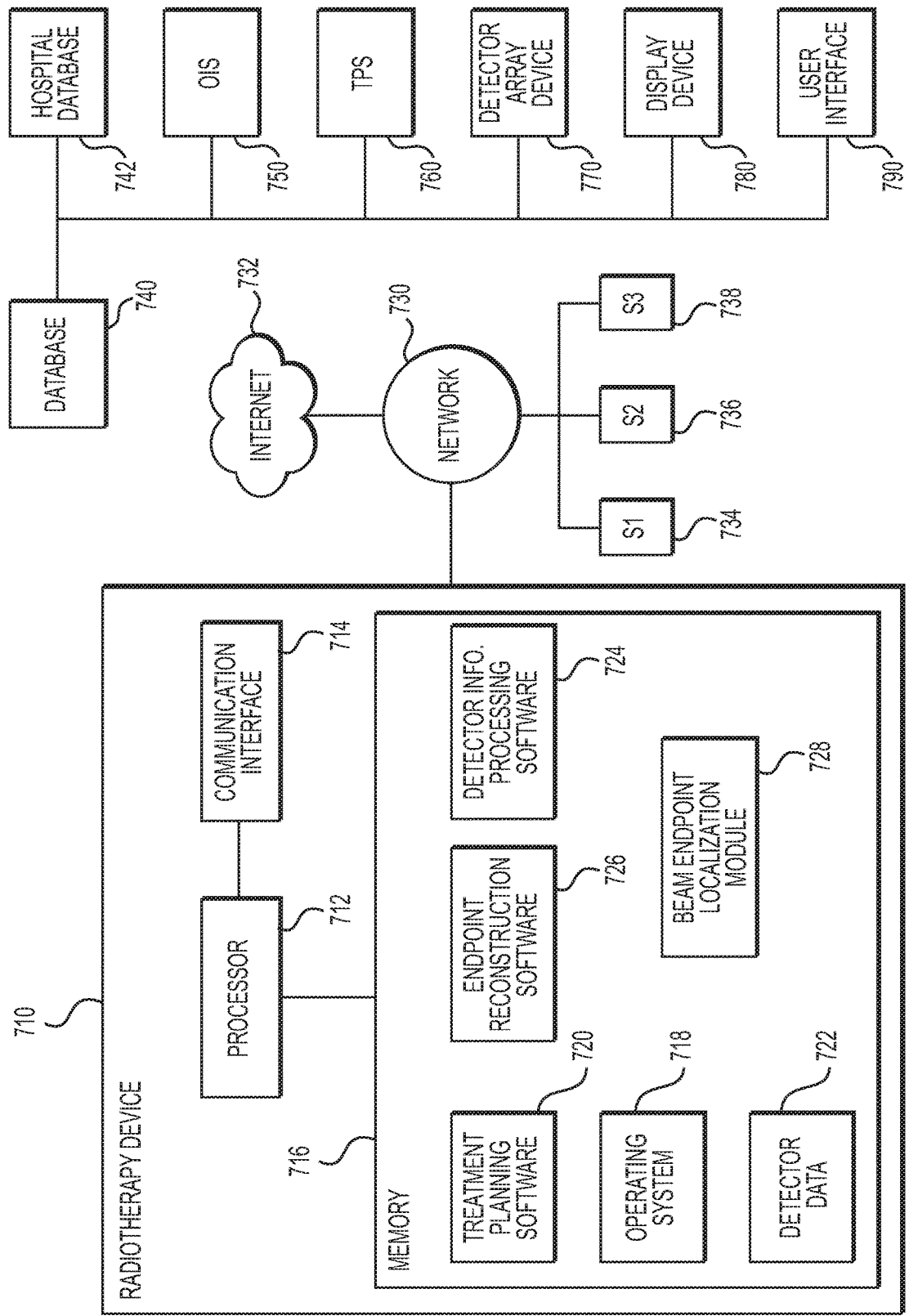
FIG. 8 depicts an exemplary system that may be used to provide real-time charged particle beam end point detection, in accordance with embodiments of the present disclosure.

The processing of information measured by detector array 114 disclosed herein may be carried out on any suitable computer and/or medical system. FIG. 8 illustrates an exemplary radiotherapy system 700 for performing real-time charged particle beam end point localization and tracking during radiation therapy treatment using the novel techniques described above. Radiotherapy system 700 may include a radiation therapy device 710 connected to a network 730 that is connected to an Internet 732. Network 730 may connect radiation therapy device 710 with one or more of a database 740, a hospital database 742, an oncology information system (OS) 750 (e.g., which may include patient information), a treatment planning system (TPS) 760 (e.g., for generating radiation therapy treatment plans to be carried out by the radiotherapy device 710), a detector array device 770, a display device 780, and/or a user interface 790. Each of these components may be housed in the same region as radiotherapy device 710 or may be remote from radiotherapy device 710, for example, connected to radiotherapy device 710 by the Internet or network connection.

Radiotherapy device 710 may include a processor 712, a memory device 716, and a communication interface 714. Memory device 716 may store computer executable instructions for one or more of an operating system 718, treatment planning software 720, detector information processing software 724, beam end point reconstruction software 726, a beam end point localization module 728, and/or any other computer executable instructions to be executed by processor 712. These executable instructions may configure processor 712 to execute the steps of the exemplary embodiments described above, including, e.g., calculation of beam end point locations, the calculation of a best fit depth for each beam end point location, a comparison of the actual or best fit beam end point locations relative to the expected beam end point locations, updating positions of the beam end points in the plan as-delivered, recalculating the dose distribution for the current or future fractions, updating the current or future treatment plan, and/or updating the stopping power map.

Processor 712 may be communicatively coupled to memory device 716, and processor 712 may be configured to execute computer executable instructions stored thereon. For example, processor 712 may execute detector information processing software 724 and/or end point reconstruction software 726 to implement functionalities of each and may combine these with the functionalities of beam end point localization module 728 in order to determine locations of the end points of a series of charged particle beams delivered to a patient during administration of radiotherapy. In addition, processor 712 may execute treatment planning software 720 (e.g., Monaco® software manufactured by Elekta) that may interface with detector processing software 724, end point reconstruction software 726, and/or beam end point localization module 728.

Processor 712 may be a processing device, include one or more general-purpose processing devices such as a microprocessor, central processing unit (CPU), graphics processing unit (GPU), an accelerated processing unit (APU), or other suitable equipment. In some embodiments, processor 712 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 712 may also be one or more special-purpose processing devices, such as an application specific integrated circuit (ASIC), a field programmable gate array (FPGA), a digital signal processor (DSP), a System on a Chip (SoC), or the like. As would be appreciated by those skilled in the art, in some embodiments, processor 712 may be a special-purpose processor, rather than a general-purpose processor, for example, one typically used for medical imaging and/or radiotherapy, and therefore may have one or more graphical processing units and accelerated processing units. Processor 712 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems, or other suitable processors. Processor 712 may also include graphical processing units, such as a GPU from the GeForce®, Quadro®, Tesla® family manufactured by Nvidia™, GMA, Iris™ family manufactured by Intel™, or the Radeon™ family manufactured by AMD™, or other suitable processors. Processor 712 may in some embodiments include accelerated processing units such as the Desktop A-4(6, 8) Series manufactured by AMD™ or the Xeon Phi™ family manufactured by Intel™. In one embodiment, processor 712 may be configured to process large amounts of data from detector array device 770 (which may be part of radiotherapy system 102) in real time, where "real time" means that the input data is processed at a speed that allows output or feedback to be made available during a radiotherapy procedure. The disclosed embodiments are not limited to any type of processor(s) otherwise configured to meet the computing demands of identifying, analyzing, maintaining, generating, and/or providing large amounts of detection and/or imaging data or manipulating such detection and/or imaging data to localize and track beam end point locations or to manipulate any other type of data consistent with the disclosed embodiments. In addition, the term "processor" may include more than one processor, for example, a multi-core design or a plurality of processors each having a multi-core design. Processor 712 may execute sequences of computer program instructions stored in memory 716 to perform the various operations, processes, and methods described above.

Memory device 716 may store detector data 722 received from detector array device 770. Memory device 716 may also store any other suitable type of data/information in any format that may be used by radiotherapy device 710 to perform operations consistent with the disclosed embodiments. Memory device 716 may include a read-only memory (ROM), a flash memory, a random access memory (RAM), a dynamic random access memory (DRAM), such as synchronous DRAM (SDRAM) or Rambus DRAM, a static memory (e.g., flash memory, static random access memory), etc., on which computer executable instructions may be stored in any format. In an exemplary embodiment, memory device 716 may be a plurality of memory devices. In some embodiments, memory device 716 may include a plurality of memory devices that are remotely located but accessible to processor 712. The computer program instructions may be accessed by processor 712, read from the ROM, or any other suitable memory location, and loaded into the RAM for execution by processor 712. For example, memory 716 may store one or more software applications. Software applications stored in memory 716 may include, for example, an operating system 718 for common computer systems, as well as for software-controlled devices. Further, memory 716 may store an entire software application or only a part of a software application that is executable by processor 712. For example, memory device 716 may store one or more radiation therapy treatment plans generated by treatment planning system 760 and/or may store treatment planning software 720.

In some embodiments, memory device 716 may include a machine-readable storage medium. Exemplary embodiments may include a single medium or may include multiple media (e.g., a centralized or distributed database, and/or associated caches and servers) that store the one or more sets of computer executable instructions or data. The term "machine-readable storage medium" refers to any medium that is capable of storing or encoding a set of instructions for execution by the machine and that cause the machine to perform any one or more of the methodologies of the present disclosure. The term "machine readable storage medium" shall accordingly be defined as including, but not be limited to, solid-state memories, optical and magnetic media, or the like. For example, memory 716 may be one or more volatile, non-transitory, or non-volatile tangible computer-readable media.

Radiotherapy device 710 may communicate with a network 730 via a communication interface 714, which may be communicatively coupled to processor 712 and memory 716. Communication interface 714 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), or other suitable connections. Communication interface 714 may include one or more digital and/or analog communication devices that permit radiotherapy device 710 to communicate with other machines and devices, such as remotely located components, via a network 730.

Network 730 may provide the functionality of a local area network (LAN), a wireless network, a cloud computing environment (e.g., software as a service, platform as a service, infrastructure as a service, etc.), a client-server, a wide area network (WAN), or the like. Therefore, network 730 may allow data transmission between radiotherapy device 710 and a number of other devices, including TPS 760, OIS 750, and detector array device 770. Further, data generated by TPS 760, OIS 750, and detector array device 770 may be stored in memory 716, database 740, and/or hospital database 742. The data may be transmitted/received via network 730 and through communication interface 714 in order to be accessed by processor 712.

Figure 9:
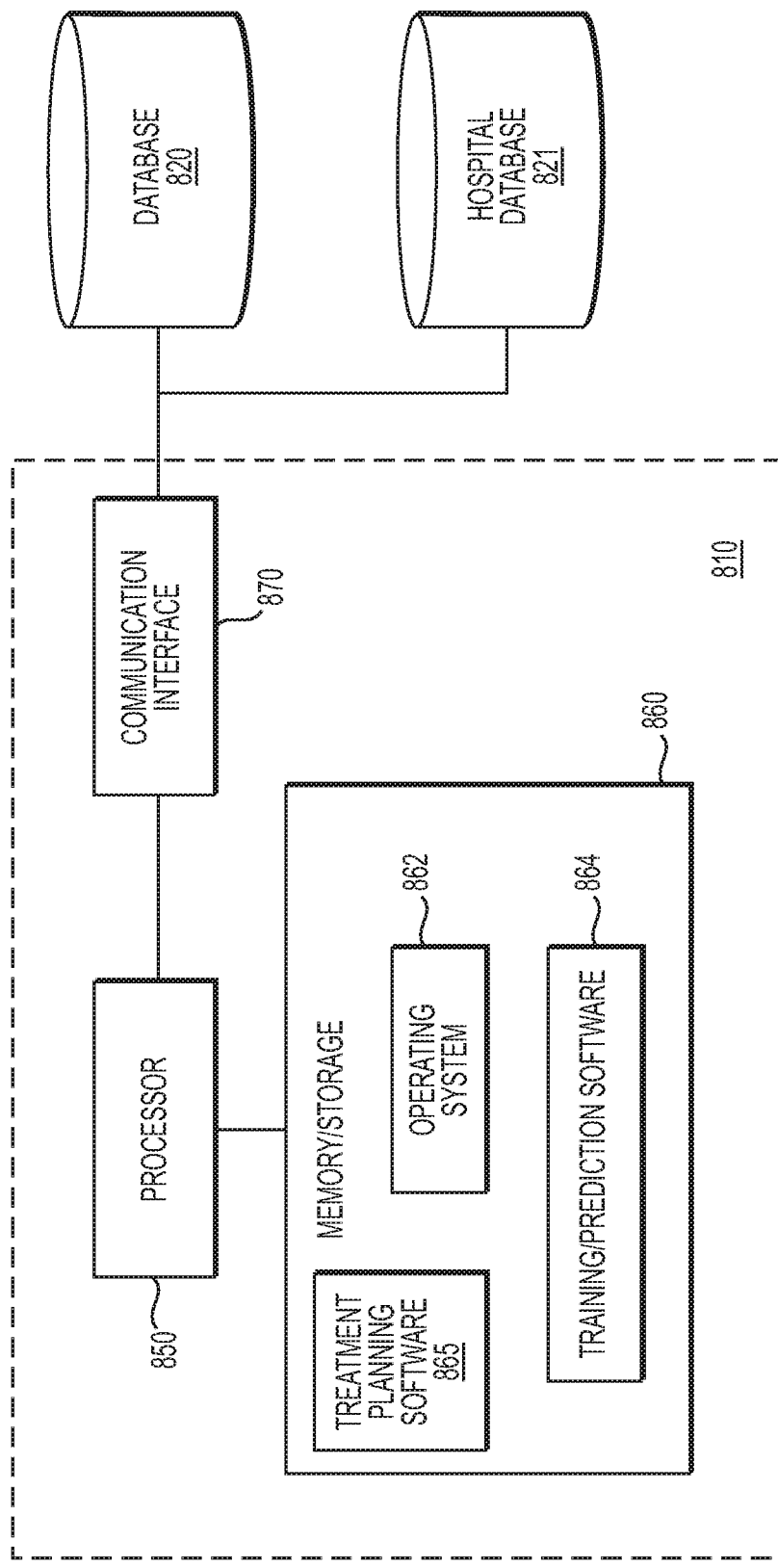
FIG. 9 depicts an exemplary system that may be used to provide real-time charged particle beam end point detection, in accordance with embodiments of the present disclosure.

FIG. 9 depicts another exemplary data processing system that may be used to carry out the processing of information generated from detector array 114 and/or comparison of the detected charged particle beam end points relative to the expected end points. FIG. 9 illustrates an embodiment of data processing device 810 that is communicatively coupled to a database 820 and a hospital database 821. As shown in FIG. 9, data processing device 810 may include a processor 850, a memory or storage device 860, and a communication interface 870. Memory/storage device 860 may store computer executable instructions, such as an operating system 862, training/prediction software 864, treatment planning software 865, and any other computer executable instructions to be executed by the processor 850.

Processor 850 may be communicatively coupled to a memory/storage device 860 and configured to execute the computer executable instructions stored thereon. For example, processor 850 may execute training/prediction software 864 to implement functionalities of the embodiments described herein. In addition, processor device 850 may execute treatment planning software 865 (e.g., such as Monaco® software manufactured by Elekta) that may interface with training/prediction software 864.

Processor 850 may communicate with database 820 through communication interface 870 to send/receive data to/from database 820. One skilled in the art would appreciate that database 820 may include a plurality of devices located either in a central or distributed manner. In addition, processor 850 may communicate with the hospital database 821 to implement functionalities of radiation therapy system 102, as shown in FIG. 1.

Processor 850 may be a processing device and may include one or more general-purpose processing devices such as a microprocessor, central processing unit (CPU), graphics processing unit (GPU), or the like. More particularly, processor device 850 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 850 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor 850 may be a special-purpose processor, rather than a general-purpose processor.

Memory/storage device 860 may include a read-only memory (ROM), a flash memory, a random access memory (RAM), a static memory, etc. In some embodiments, memory/storage device 860 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that cause the machine to perform any one or more of the methodologies of the present disclosure. The term "machine readable storage medium" shall accordingly be taken to include, but not be limited to, solid-state memories, optical, and magnetic media.

Communication interface 870 may include a network adaptor, a cable connector, a serial connector, a USB connector, a parallel connector, a high-speed data transmission adaptor such as fiber, USB 3.0, thunderbolt, a wireless network adaptor such as a WiFi adaptor, or a telecommunication (3G, 4G/LTE and the like) adaptor. The communication interface 870 may provide the functionality of a local area network (LAN), a wireless network, a cloud computing environment (e.g., software as a service, platform as a service, infrastructure as a service), a client-server, or a wide area network (WAN). Processor 850 may communicate with database 820 or other devices or systems via communication interface 870.

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A system for measuring an end point of a charged particle beam during radiotherapy treatment, the system comprising:
   at least one computer system configured to:
      receive a signal indicative of a magnetic field detected by a plurality of detectors arranged along an axis that is parallel to a beam axis along which the charged particle beam is delivered and each individual detector of the plurality of detectors is configured to detect whether the charged particle beam extends along the beam axis to a location of that individual detector;

based on the received signal, determine an in vivo location of the end point of the charged particle beam; and continue, modify, or stop the radiotherapy treatment based on the in vivo location of the end point of the charged particle beam.

2. The system of claim 1, wherein the at least one computer system is further configured to:

compare the in vivo location of the end point of the charged particle beam to an intended location of the end point of the charged particle beam calculated prior to delivery of the charged particle beam.

3. The system of claim 2, wherein the at least one computer system is further configured to:

stop or modify the radiotherapy treatment if the in vivo location of the end point of the charged particle beam is outside of a threshold level of error relative to the intended location of the end point of the charged particle beam; and continue the radiotherapy treatment if the in vivo location of the end point of the charged particle beam is within the threshold level of error relative to the intended location of the end point of the charged particle beam.

4. The system of claim 2, wherein the at least one computer system is further configured to:

update at least one of a stopping power map, a record of a plan as-delivered, or a treatment record to include the in vivo location of the end point of the charged particle beam.

5. The system of claim 2, wherein the at least one computer system is further configured to:

modify a future radiotherapy treatment session based on the in vivo location of the end point of the charged particle beam.

6. The system of claim 1, wherein the charged particle beam is a proton beam.

7. The system of claim 1, wherein the plurality of detectors comprises at least one of a superconducting quantum interference device, a laser-pumped detector, or a magnetometer.

8. The system of claim 1, wherein at least one detector of the plurality of detectors is oriented so that a planar surface of the at least one detector is oriented at an angle transverse to the axis that is parallel to the beam axis.

9. The system of claim 1, wherein the plurality of detectors is interdigitated.

10. The system of claim 1, wherein the plurality of detectors form part of a detector array.

11. The system of claim 10, wherein the detector array is a two-dimensional detector array.

12. The system of claim 10, wherein the plurality of detectors is movably mounted on the detector array.

13. The system of claim 10, wherein the plurality of detectors also extend along a width of the detector array.

14. The system of claim 10, further comprising a plurality of detector arrays.

15. The system of claim 10, wherein the detector array is a first detector array, and the system further comprises a second detector array.

16. The system of claim 15, wherein the second detector array is positioned orthogonal to the first detector array.

17. A method of measuring an end point of a charged particle beam during radiotherapy treatment, the method comprising:

receiving a signal indicative of a magnetic field detected by a plurality of detectors arranged along an axis that is parallel to a beam axis along which the charged particle beam is delivered and each individual detector of the plurality of detectors is configured to detect whether the charged particle beam extends along the beam axis to a location of that individual detector;

based on the received signal, determining an in vivo location of the end point of the charged particle beam; and continuing, modifying, or stopping the radiotherapy treatment based on the in vivo location of the end point of the charged particle beam.

18. The method of claim 17, comprising:

comparing the in vivo location of the end point of the charged particle beam to an intended location of the end point of the charged particle beam calculated prior to delivery of the charged particle beam.

19. The method of claim 18, comprising:

stopping or modifying the radiotherapy treatment if the in vivo location of the end point of the charged particle beam is outside of a threshold level of error relative to the intended location of the end point of the charged particle beam; and continuing the radiotherapy treatment if the in vivo location of the end point of the charged particle beam is within the threshold level of error relative to the intended location of the end point of the charged particle beam.

20. The method of claim 18, comprising:

updating at least one of a stopping power map, a record of a plan as-delivered, or a treatment record to include the in vivo location of the end point of the charged particle beam.

21. The method of claim 18, comprising:

modifying a future radiotherapy treatment session based on the in vivo location of the end point of the charged particle beam.

* * * * *